United States Patent [19]

Gossett et al.

[11] Patent Number: 5,426,110
[45] Date of Patent: Jun. 20, 1995

[54] PYRIMIDINYL-GLUTAMIC ACID DERIVATIVES

[75] Inventors: Lynn S. Gossett, Indianapolis; Chuan Shih, Carmel, both of Ind.

[73] Assignee: Eli Lilly and Company, Indianapolis, Ind.

[21] Appl. No.: 132,514

[22] Filed: Oct. 6, 1993

[51] Int. Cl.$^6$ ............... A61K 31/505; C07D 239/42; C07D 239/48; C07D 401/12
[52] U.S. Cl. ................................ 514/275; 514/272; 544/320; 544/321; 544/324; 544/325; 544/331; 544/332
[58] Field of Search ............... 514/275, 272; 544/321, 544/332, 320, 324, 325, 331

[56] References Cited

U.S. PATENT DOCUMENTS

| | | | |
|---|---|---|---|
| 4,684,653 | 8/1987 | Taylor et al. | 514/258 |
| 4,871,743 | 10/1989 | Taylor et al. | 514/272 |
| 4,920,125 | 4/1990 | Taylor et al. | 514/272 |

OTHER PUBLICATIONS

Weinstock, et al., *J. Med. Chem.* 11(6):1238-1241 (1968).
Stuart, et al., *J. Med. Chem.*, 26:667-673 (1983).
Taylor, et al., *Heterocycles*, 28(2):1169-1178 (1989).
Taylor et al., Chemical Abstracts, vol. 117, entry 212902e (1992).
Taylor et al., Chemical Abstracts, vol. 116, entry 152317k (1992).
Akimoto et al, Chemical Abstracts, vol. 115, entry 29364a (1990).

*Primary Examiner*—John M. Ford
*Attorney, Agent, or Firm*—Robert A. Conrad; Steven A. Fontana; David E. Boone

[57] ABSTRACT

The present invention provides novel pyrimidinyl-glutamic acid derivatives and intermediates thereto. Further provided are methods for inhibiting dihydrofolate reductase in mammals and for treating susceptible neoplasms in mammals, particularly humans.

43 Claims, No Drawings

PYRIMIDINYL-GLUTAMIC ACID DERIVATIVES

BACKGROUND OF THE INVENTION

The folic acid antimetabolites aminopterin and amethopterin (also known as 10-methylaminopterin or methotrexate) are antineoplastic agents. These compounds inhibit enzymatic conversions involving metabolic derivatives of folic acid. Amethopterin, for example, inhibits dihydrofolate reductase (DHFR), an enzyme necessary for the regeneration of tetrahydrofolate from dihydrofolate which is formed during the conversion of 2-deoxyuridylate to thymidylate by the enzyme thymidylate synthetase.

Other derivatives of folic acid and aminopterin have been synthesized and tested as antimetabolites. Among these are compounds in which a methylene or methylidine group occupies a position in the molecule normally occupied by an amino or nitrilo group, respectively. These derivatives have varying degrees of antimetabolic activity. 10-Deazaaminopterin is highly active [(Sirotnak, et al., Cancer Treat. Rep., 62:1047 (1978)] and 5-deazaaminopterin has activity similar to that of amethopterin [(Tayler, et al., J. Org, Chem., 48:4842 (1983)]. 8,10-Dideazaaminopterin is reported to be antimetabolically active (U.S. Pat. No. 4,460,591) and 5,8,10-trideazaaminopterin exhibits activity against mouse L1210 leukemia [(Yan, et al., J, Heterocycl. Chem., 16:541 (1979)]. 10-Deazafolic acid, on the other hand, shows no significant activity (Struck, et al., J. Med. Chem., 14:693(1971) and 5-deazafolic acid is only weakly cytotoxic. 8,10-Dideazafolic acid is only marginally effective as a dihydrofolate reductase inhibitor [(DeGraw, et al., "Chemistry and Biology of Pteridines", Elsevier, 229 (1979)] and 5,8,10-trideazafolic acid also shows only marginal activity against mouse L1210 leukemia [(Oatis, et al., J. Med. Chem., 20:1393 (1977)]. 5,10-Dideazaaminopterin and 5,10-dideaza-5,6,7,8-tetrahydroaminopterin, and the corresponding 5,10-dideazafolic acid derivatives are reported by Taylor, et al., J, Med. Chem., 28, No. 7:914 (1985).

Additional derivatives of folic acid and aminopterin include: 10-oxafolic acid and 7,8-dihydro-10-oxafolic acid which are not effective inhibitors of DCM resistant Lactobacillus casei dihydrofolate reductase; 10-oxaaminopterin and 7,8-dihydro-10-thiofolic acid, which are potent DHFR inhibitors [(Nair, et al., J. Med. Chem., 19, No. 6:825 (1976)]; 10-thiafolic acid, a moderate DHFR inhibitor; and a very potent dihydrofolate reductase inhibitor, 10-thiaaminopterin [(Kim, et al., J. Med. Chem. 18, No. 8:776 (1975)].

The present invention provides novel "open-chain" folic acid derivatives, hereinafter referred to as pyrimidinyl-glutamic acid derivatives, intermediates for the preparation, pharmaceutical compositions, and their use for the inhibition of dihydrofolate reductase and the treatment of susceptible neoplasms in mammals.

SUMMARY OF THE INVENTION

The present invention relates to compounds of formula I

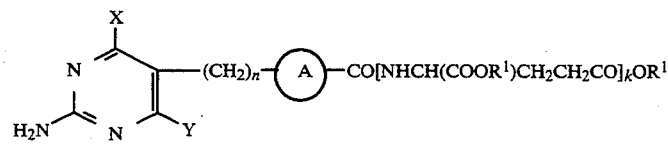

wherein
X is H, bromo, chloro, fluoro, or mercapto;
Y is $NH_2$, or $CH_3$;
n is 2 to 5;
each $R^1$ is H or the same or different carboxy protecting group;
k is 1 to 5; and
Ⓐ is an aryl group which may be substituted; or a salt or solvate thereof.

A further aspect of the present invention are intermediate compounds of formula III

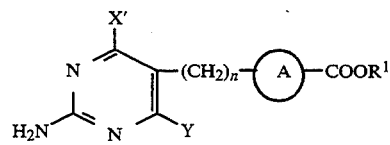

wherein
X' is bromo, chloro, or fluoro;
Y is $NH_2$ or $CH_3$;
n is 2 to 5;
Ⓐ is an aryl group which may be substituted; and
$R^1$ is H or a carboxy protecting group; or a salt or solvate thereof.

Another aspect of the present invention are compounds of formula V

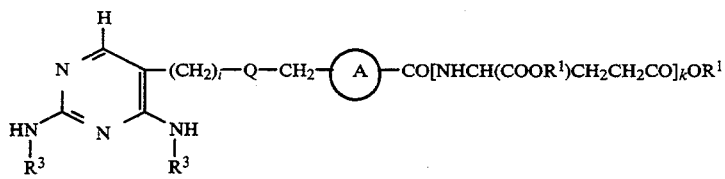

wherein
each $R^1$ is H or the same or different carboxy protecting group;
each $R^3$ is H or the same or different amino protecting group;
i is 1 to 4;
Q is —O—, —S(O)$_j$— (j is 0 to 2), or a group of the formula —$NR^2$— in which $R^2$ is H, $C_1$-$C_4$ alkyl, $C_2$-$C_4$ alkenyl, or $C_2$-$C_4$ alkynyl;
Ⓐ is an aryl group which may be substituted; and
k is 1 to 5;
or a salt or solvate thereof.

The present invention also relates to pharmaceutical compositions containing compounds of formula I, and the use of such compounds, particularly when $R^1$ is H, for inhibiting dihydrofolate reductase and the treatment of susceptible neoplasm in mammals, particularly humans.

DETAILED DESCRIPTION OF THE INVENTION

The present invention relates, in part, to compounds of formula I

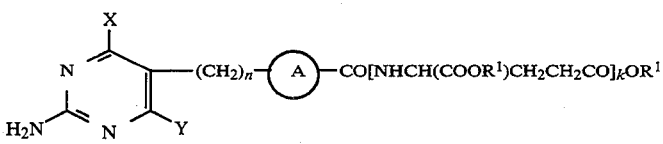

wherein
X is H, bromo, chloro, fluoro, or mercapto;
Y is $NH_2$, or $CH_3$;
n is 2 to 5;
each $R^1$ is H or the same or different carboxy protecting group;
k is 1 to 5; and
(A) is an aryl group which may be substituted; or a salt or solvate thereof.

In formulae I and V, each of the glutamic acid residues has an asymmetric center (as shown in formula I infra) and, thus, can have an L- or D-configuration. The glutamic acid residue attached directly to the aroyl functionality preferably has the L-configuration. It is especially preferred that compounds of formulae I and V have a single glutamic acid residue (k=1) which is in the L-configuration.

The term "$C_1$–$C_4$ alkyl" refers to methyl, ethyl, propyl, isopropyl, n-butyl, isobutyl, sec-butyl and tert-butyl (t-butyl); the term "$C_2$–$C_4$ alkenyl" refers to, for example, vinyl, allyl, 1-methylvinyl, 1-propenyl, 2-butenyl, and the like; and the term "$C_2$–$C_4$ alkynyl" refers to, for example, ethynyl, 1-propynyl, propargyl, and the like.

The term "an aryl group which may be substituted", as used in describing the ring structure identified as (A), refers to 5- to 6-membered aromatic residues, including heterocyclic groups containing up to three heterotoms (e.g., N, O, and S) therein, such as, for example, phenyl, thienyl, pyridyl, furyl, and the like. Of these, phenyl, thienyl, and furyl are preferred. Such aryl groups optionally may be substituted, in addition to the substituents shown in, for example, formulae I, III, and V, with one or two substituent groups selected from halo (bromo, chloro, fluoro, and iodo), hydroxy, $C_1$–$C_4$ alkyl, and $C_1$–$C_4$ alkoxy.

The term "$C_1$–$C_4$ alkoxy" represents a $C_1$–$C_4$ alkyl group attached through an oxygen bridge, such as, for example, methoxy, ethoxy, n-propoxy, isopropoxy, and the like.

The term "amino protecting group" as used in the specification refers to substituents of the amino group commonly employed to block or protect the amino functionality while reacting other functional groups on the compound. Examples of such amino protecting groups include the formyl group, the trityl group, the phthalimido group, the trichloroacetyl group, the chloroacetyl, bromoacetyl and iodoacetyl groups, urethane-type blocking groups such as the benzoylmethylsulfonyl group, the 2-(nitro) phenylsulfenyl group, the diphenylphosphine oxide group and like amino protecting groups. The species of amino protecting group employed is not critical so long as the derivatized amino group is stable to the condition of subsequent reaction(s) on other positions of the intermediate molecule and can be selectively removed at the appropriate point without disrupting the remainder of the molecule including any other amino protecting group(s). Preferred amino protecting groups are ($C_1$–$C_4$ alkyl)carbonyl and trimethylacetyl, and most preferred is trimethylacetyl. Further examples of groups referred to by the above terms are described by J. W. Barton, "Protective Groups in Organic Chemistry", J. G. W. McOmie, Ed., Plenum Press, New York, N.Y., 1973, Chapter 2, and T. W. Greene, "Protective Groups in Organic Synthesis", John Wiley and sons, New York, N.Y., 1981, Chapter 7.

The term "carboxy protecting group" as used herein refers to one of the ester derivatives of the carboxylic acid group commonly employed to block or protect the carboxylic acid group while reactions are carried out on other functional groups on the compound. Examples of such carboxylic acid protecting groups include 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, methyl, ethyl, propyl, isopropyl, t-butyl, t-amyl, trityl, 4-methoxytrityl, 4,4'dimethoxytrityl, 4,4'4"-trimethoxytrityl, 2-phenylprop-2-yl, trimethylsilyl, t-butyldimethylsilyl, phenacyl, 2,2,2-tricholorethyl, β-(trimethylsilyl)ethyl, β-(di(n-butyl)methylsilyl-)ethyl, p-toluenesulfonylethyl, 4-nitrobenzylsulfonylethyl, allyl, cinnamyl, 1-(trimethylsilylmethyl)-prop-1-en-3-yl, and like moieties. The species of carboxy protecting group employed is not critical so long as the derivatized carboxylic acid is stable to the condition of subsequent reaction(s) on other positions of the molecule and can be removed at the appropriate point without disrupting the remainder of the molecule. Further examples of these groups are found in E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981, Chapter 5. A related term is "protected carboxy", which refers to a carboxy group substituted with one of the above carboxy protecting groups. Preferred protecting groups are methyl and ethyl, and t-butyl is especially preferred.

As mentioned above, the invention includes salts of the compounds defined by the above formulae. A particular compound of this invention can possess a sufficiently acidic, a sufficiently basic, or both functional groups, and accordingly react with any of a number of inorganic bases, and inorganic and organic acids, to form a pharmaceutically acceptable salt. Acids commonly employed to form acid addition salts are inorganic acids such as hydrochloric acid, hydrobromic acid, hydroiodic acid, sulfuric acid, phosphoric acid, and the like, and organic acids such as p-toluene-sulfonic, methanesulfonic acid, oxalic acid, p-bromo-phenyl-sulfonic acid, carbonic acid, succinic acid, citric acid, benzoic acid, acetic acid, and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycollate, tartrate, methanesulfonate, propanesulfonate, naphthalene-1-sulfonate, naphthalene-2-sulfonate, mandelate, and the like. Preferred pharmaceutically acceptable acid addition salts are those formed with mineral acids such as hydrochloric acid and hydrobromic acid, and those formed with organic acids such as maleic acid and methanesulfonic acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate. The potassium and sodium salt forms are particularly preferred.

Of course, when the intermediates of this invention are converted to final, pharmaceutically active compounds (compounds of formula I in which $R^1$ is H), those compounds may also be in the form of a salt. However, the salt of the final compounds must be of the pharmaceutically acceptable nature.

Processes for preparing acid addition, base addition, and pharmaceutically acceptable salts (salification) are well known in the art. Compounds of formula I are prepared via various processes.

In one process, the starting material is a compound of formula IIa

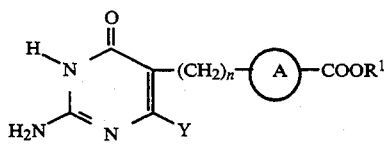

wherein Y, n, (A), and $R^1$ are as defined above.

Formula IIa compounds in which n is 2 to 5, $R^1$ is H, and (A) is phenyl or thienyl are taught by Taylor, et al., U.S. Pat. Nos. 4,871,743 and 4,920,125, respectively, which are herein incorporated by reference. Compounds of formula IIa in which n is 4 and (A) is benzyl are taught by Taylor, E. C., et al., *Heterocycles*, 28(2):1169–1178 (1989).

In preparing formula I In compounds, however, one skilled in the art can readily replace the (A) groups taught by Taylor with optionally substituted aryl groups commensurate with the above definition. One skilled in the art also may protect the carboxylic acid functionality as taught by Taylor or by other means known in the art.

The first step of the present process for preparing the pyrimidinyl compounds of the present invention requires reacting a compound of formula IIa with a chlorinating or brominating agent in the presence of an inert or substantially inert solvent or mixture of solvents. The resulting product, compounds of formula IIIa, are novel and are useful intermediates for the preparation of formula I compounds.

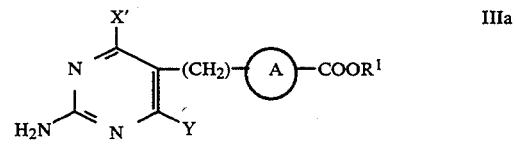

wherein
X' is bromo, chloro, or fluoro; and
Y, n, (A), and $R^1$ are as defined above; or a salt or solvate thereof.

Suitable brominating agents and chlorinating agents are any compound which releases bromide and chloride ions, respectively. Preferred brominating agents are phosphorous oxybromide and phosphorous tribromide; and preferred chlorinating agents are $PCl_3$ and, especially, $POCl_3$.

The amount of brominating or chlorinating agent employed in this reaction is an amount sufficient to displace the 4-oxo group (or its OH tautomer) with the respective halogen. Generally, from about one equivalent to an excess of the respective halogenating agent per equivalent of the substrate is used. Preferably, an excess of the respective halogenating agent is used.

The temperature employed in the seep is sufficient to effect completion of the reaction. The temperature is generally from about room temperature to about reflux. Preferably, this reaction is run at about 90° C. to reflux.

The length of time for the first step can be any that is required for the displacement to occur. The reaction generally requires from about 3 to about 7 hours. The optional reaction time can be determined by monitoring the progress of the reaction by conventional chromatographic techniques such as thin layer chromatography, high performance liquid chromatography, or column chromatography.

Optionally, formula IIIa compounds in which X' is chloro may be fluorinated via methods known in the art [see, e.g., Ratsep, P. C., et al., *Nucleosides and Nucleotides*, 9(2):197–204 (1990)]. The product of this fluorination step is a compound of formula IIIa in which X' is fluoro.

In the next step of the present process, a formula IIIa compound is coupled with a protected glutamic acid derivative of formula IV

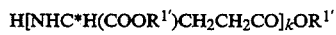

wherein each $R^{1'}$ is the same or different carboxy protecting group and k is 1 to 5, using conventional condensation techniques for forming peptide bonds. These techniques generally are known in the art and are described, for example, by Taylor, et al., in U.S. Pat. No. 4,684,653 which is herein incorporated by reference.

The resulting product of this condensation step is a compound of formula Ia

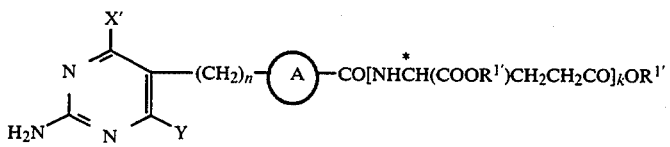

Ia wherein X', Y, n, e,crc/A/, R¹, and k are as defined above, and the carbon atom designated * represents an asymmetric center, or a salt or solvate thereof. Compounds of formula Ia are novel intermediates and are useful for the preparation of pharmaceutically active, final compounds of formula I in which each R¹ is H.

As mentioned above, each R¹' may be the same or different carboxy protecting group, such groups being well known in the art. It is preferred, however, that each R¹ is the same carboxy protecting group, while preferred R¹ groups include methyl, ethyl and, especially, t-butyl.

As mentioned above, the configuration of each glutamic acid residue of compounds of the present invention may either be L- or D-. Preferably, when k is greater than 1, the glutamic acid residue attached to the aroyl moiety of formula I compounds is in the L-configuration. Especially preferred are formula I compounds in which k is 1 and the single glutamic acid residue is in the L-configuration.

Formula Ia compounds next may be converted into final, therapeutically active compounds or may be converted into other novel intermediates which also are useful for the preparation of their corresponding final compounds. These options are depicted below in Scheme I.

in the presence of an appropriate hydrogenation catalyst, and hydrogenated with hydrogen gas.

Suitable solvents include any solvent or mixture of solvents which will remain inert under hydrogenation conditions. Suitable solvents include, for example, glucial acetic acid and alcohols such as methanol, ethanol, 1-propanol, and 2-propanol. The most preferred solvent is glucial acetic acid.

The hydrogenation catalyst can be any material which contains a noble metal and will catalyze the present hydrogenation step. Examples of suitable catalysts include noble metals supported on alkaline earth carbonates. Noble metals herein refer to gold, silver, platinum, palladium, iridium, rhodium, mercury, ruthenium, and osmium. Preferred catalysts include palladium-on-carbon, platinum-on-carbon, palladium oxide, and palladium black. The most preferred hydrogenation catalyst is palladium black.

The temperature and pressure employed in this step are those sufficient to effect completion of the hydrogen reaction. Temperatures in the range from about 30° C. to about 150° C. will suffice while a temperature in the range from about 50° C. to about 70° C. is preferred. Pressures employed are from about 10 psi to about 200 psi.

Alternatively, formula Id compounds are prepared

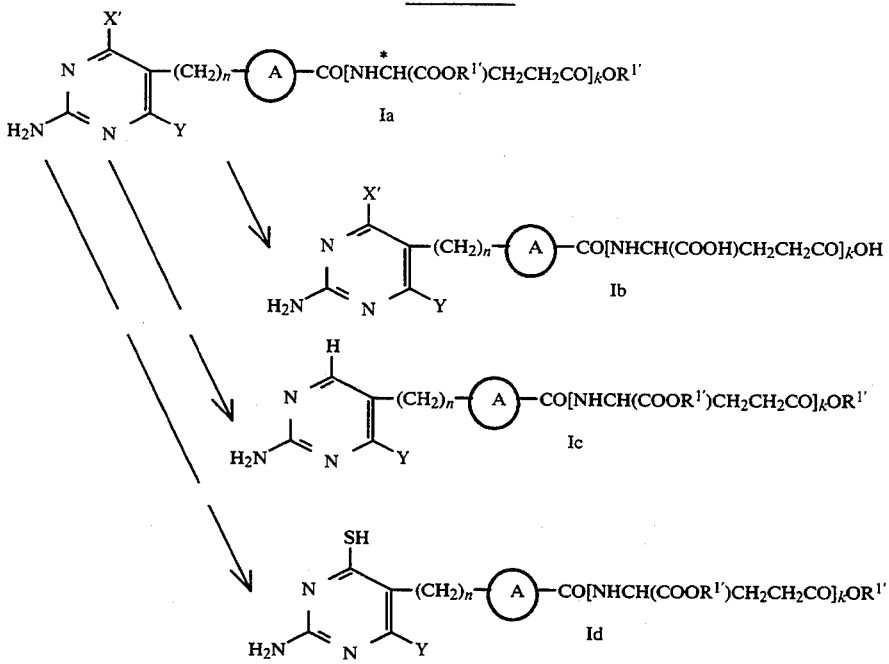

Scheme I wherein X', Y, n, (A), and R¹' are as defined above, or a salt or solvate thereof.

Formula Ic compounds are prepared via catalytic hydrogenation of a compound of formula Ia. Typically a formula Ia compound is dissolved in a suitable solvent by displacing the 4-position bromo or chloro functionality of a formula Ia compound with a 4-mercapto functionality. This process is accomplished by reacting a formula Ia compound, preferably when X' is chloro, with a sulfur containing nucleophile such as, for example, thiourea, methanethiol, ethanethiol, thiophenol and the like, in the presence of a suitable solvent, This reaction generally is known in the art as exemplified by March, *Advanced Organic Chemistry: Reactions, Mechanisms, and Structure*, McGraw-Hill, 1st ed., p. 500.

The solvent employed in this step is any solvent or mixture of solvents which will remain inert under these reaction conditions. The preferred solvent is 2-methoxyethanol.

The final step in preparing final, therapeutically active compounds from the above-described process involves removing the carboxy protecting groups ($R^{1'}$) from compounds of formulae Ia (to give a compound of above-depicted Ib) Ic, and Id via basic or acid hydrolysis. This process yields compounds of formula I which are useful as therapeutic agents as herein described. Specific method for removing the carboxy protecting groups are described in the standard references which previously are noted.

The present application also provides compounds of formula V

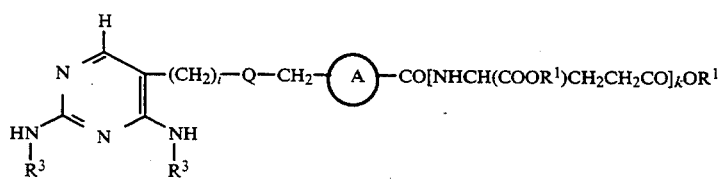

wherein
each $R^1$ is H or the same or different carboxy protecting group;
each $R^3$ is H or the same or different amino protecting group;
i is 1 to 4;
Q is —O—, —S(O)$_j$— (j is 0 to 2), or a group of the formula —NR$^2$— in which $R^2$ is H, $C_1$–$C_4$ alkyl, $C_2$–$C_4$ alkenyl, or $C_2$–$C_4$ alkynyl;
Ⓐ is an aryl group which may be substituted; and
k is 1 to 5;
or a salt or solvate thereof.

For the preparation of formula V compounds in which Q is a group of the formula —NR$^2$—, one of the starting materials is a compound of formula VI. The 2- and 6-position amino groups are first protected, providing compounds of formula VII, and the 5-position carbon is alkylated to provide the desired length of the alkylene bridge, giving compounds of formula VIII. This aspect of the present process is shown in Scheme II.

Scheme II

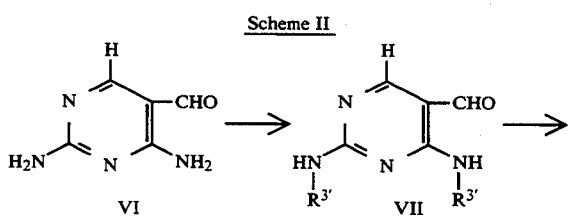

-continued
Scheme II

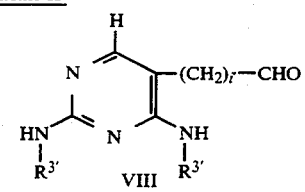

wherein each $R^{3'}$ is the same or different amino protecting group and i' is 1 to 3.

Preparation of the formula VI compound is known in the art (see, Stuart, A., et al., *J. Med. Chem.*, 26:667–673 (1983). Protection of the 2- and 6-position amino groups of formula VI can be accomplished via various well known methods. Although each amino group may have different protecting groups, it is preferred that each $R^{3'}$ functionality is the same group. The preferred protecting group for each $R^{3'}$ is pivaloyl.

Alkylation of the 5-position carbon atom of formula VII compounds provides the desired alkylene bridge length between the pyrimidinyl moiety and the aldehyde moiety of formula VIII. This alkylation step is well known in the art and can provide up to 4 additional methylene groups in the alkylene bridge. The preferred length of this bridge is 1 or 2 methylene groups while 1 methylene group (i=1) is especially preferred.

The other starting material for preparing compounds of formula V in which the Q is —NR$^2$— and $R^2$ is H, $C_1$–$C_4$ alkyl, $C_2$–$C_4$ alkenyl, or $C_1$–$C_4$ alkynyl is a compound of formula IX.

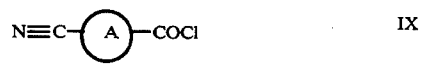

wherein Ⓐ is a defined above. Compounds of formula IX are well known and, to the extent not commercially available, are readily synthesized by standard procedures commonly employed by those of ordinary skill in the art.

A formula IX compound is then coupled with a protected glutamic acid derivative as described above, to form a compound of formula X, which is then catalytically hydrogenated to form a formula XI compound, and optionally substituted to form compounds in which $R^2$ is $C_1$–$C_4$ alkyl, $C_2$–$C_4$ alkenyl, or $C_2$–$C_4$ alkynyl (compounds of formula XII). A compound of formula XII or, preferably, formula XI is then condensed with a compound of formula VII to provide the novel intermediates of formula Va. Formula Va compounds are deprotected to provide the novel, pharmaceutically active compounds of formula Vb. This aspect of the present process is depicted in Scheme III.

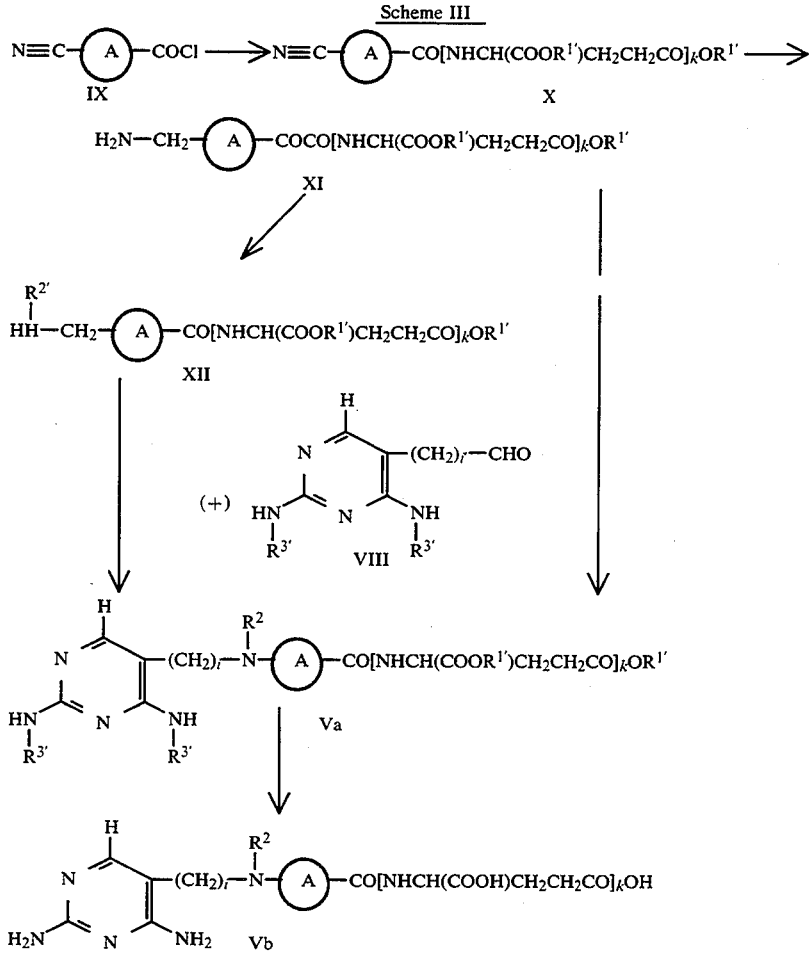

Scheme III wherein
each $R^{1'}$ is the same or different carboxy protecting group;
$R^{2'}$ is $C_1$-$C_4$ alkyl, $C_2$-$C_4$ alkenyl, or $C_2$-$C_4$ alkynyl;
$R^2$ is H, $C_1$-$C_4$ alkyl, $C_2$-$C_4$ alkenyl, or $C_2$-$C_4$ alkynyl;
each $R^{3'}$ is the same or different amino protecting group;
$i'$ is 1 to 3;
$i$ is 1 to 4;
Ⓐ is an aryl group which may be substituted; and
$k$ is 1 to 5;
or a salt or solvate thereof.

The coupling of a formula IX compound with a formula IV glutamic acid derivative generally is discussed supra. Typically, the desired glutamic acid derivative is dissolved in an inert solvent or mixture of solvents, preferably anhydrous methylene chloride, in the presence of an acid scavenger such as triethylamine, under a gas atmosphere such as nitrogen gas. To this solution is added a solution of the desired formula IX compound dissolved in an inert solvent or mixture of solvents. The preferred solvent is anhydrous methylene chloride.

The resulting product of this reaction, a compound of formula X, is then catalytically hydrogenated. The product of this hydrogenation reaction is depicted as a compound of formula XI. Although numerous catalysts and solvents are appropriate for this reaction, it is preferred to use palladium-on carbon and glacial acetic acid respectively. The amount of reactants and the temperature necessary for running this reaction are known to one of ordinary skill in the art.

Following hydrogenation, a compound of formula XI may be condensed with a compound of formula VIII via known procedures to form a Schiff's base, which must later be reduced to form a compound of formula Va, or via reductive amination.

Preferably, a compound of formula XI and a compound of formula VIII, are dissolved in a suitable solvent, followed by the dropwise addition of an appropriate reducing agent.

Suitable solvents can be any solvent or mixture of solvents which will remain inert under the condensation conditions. Such solvents include glacial acetic acid and alcohols such as methanol, ethanol, 1-propanol, and 2-propanol. The most preferred solvent is absolute ethanol.

Appropriate reducing agents are well known in the art and include, for example, hydrogen and an appropriate catalyst, zinc and HCl, sodium cyanoborohydride, sodium borohydride, diborane, and the like. Of these, sodium borohydride is preferred.

The amount of a formula XI compound employed in this reaction is generally an amount sufficient to react with all of the compound of formula VIII present. Typically, equivalent amounts of reactants are used.

The temperatures used in this reaction are sufficient to run this reaction to completion and generally are from about 0° C. to ambient temperature. Preferably, this condensation reaction is run at ambient temperature while the reduction is completed near 0° C.

The length of time for this step is that amount necessary for the reaction to occur. Typically, this reaction requires from about 3 hours to about 9 hours. The optimal time can be determined by monitoring the progress of the reaction via the above-mentioned conventional chromatographic techniques.

Alternatively, the primary amine of formula XI compounds are first alkylated, alkenylated, or alkynylated, via standard procedures to form compounds of formula XII, and then coupled with a compound of formula VIII via reductive amination to provide compounds of formula Va. Preferred reducing agents for this known reaction (see, e.g., March, J., supra) include for example, sodium cyanoborohydride, sodium borohydride, and diborane.

Compounds of formula Va are novel intermediates for the preparation of final, pharmaceutically active compounds of the present invention. To convert formula Va compounds to final compounds of formula Vb, each $R^1$ and each $R^3$ of formula Va compounds are deprotected using basic hydrolysis. Method of removing the various protecting groups are described in the above-referenced literature.

Compounds of formula V in which Q is a heteroatom other than nitrogen also are provided by the present invention.

One of the starting materials for this preparation is a compound of formula VIII which first is reduced to form a compound of formula XIII, the alcohol functionality of which is then substituted with a leaving group ($R^4$) to provide compounds of formula XIV. These reactions are depicted in Scheme IV.

Scheme IV

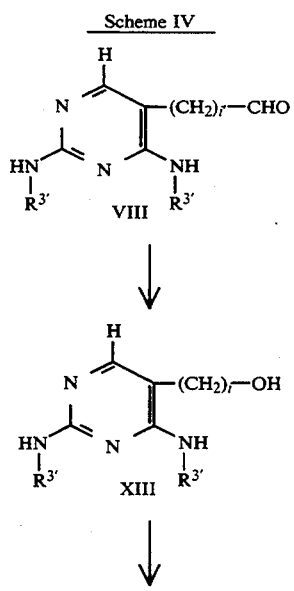

-continued
Scheme IV

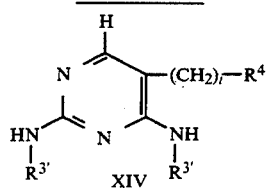

wherein
each $R^{3'}$ is the same or different amino protecting group;
$i'$ is 0 to 3;
$i$ is 1 to 4; and
$R^4$ is a leaving group.

Both of the reactions shown in Scheme IV are well known to an organic chemist of ordinary skill (see, e.g., March, J., supra).

For the first step, commonly used reducing agents such as, for example, sodium borohydride, sodium cyanoborohydride, and the like may be employed.

Any one of a number of leaving groups are appropriate for the second step of this reaction scheme such as, for example, the sulfonates including methanesulfonate, 4-bromobenzenesulfonate, 4-methoxybenzenesulfonate, 4-nitrobenzenesulfonate, 2-chlorobenzenesulfonate, triflate, and the like, and other related leaving groups. Preferred leaving groups are methanesulfonate and bromo.

The second primary reactant for preparing compounds of formula V in which Q is other than —$NR^2$— is a compound of formula XV

wherein
$Q'$ is HO— or $HS(O)_j$— (j is 0 to 2); and
(A), $R^{1'}$ and k are as defined above;
or a salt or solvate thereof.

Compounds of formula XV can be prepared via well known procedures using commercially available materials and, to the extent no commercially available, materials which are readily prepared by standard procedures commonly employed by those of ordinary skill in the art.

For example, commercially available p-toluic acid, 5-methylfurfural, t-methylthiophene-2-carboxaldehyde, or the like (formula XVI) is converted to its respective aldehyde (formula XVII), which is then reduced to the alcohol of formula XVIII. A formula XVIII compound is then either condensed with a glutamic acid derivative of formula IV to form a compound of formula XVa or the alcohol functionality is substituted with a leaving group (formula XIX which is then, for example, thiolated to form a formula XX compound. A formula XX compound is then coupled with a glutamic acid derivative of formula IV to give a compound of XVb, which is reacted with a formula XIV compound to provide the intermediates of formula Vc. These reactions are depicted in Scheme V.

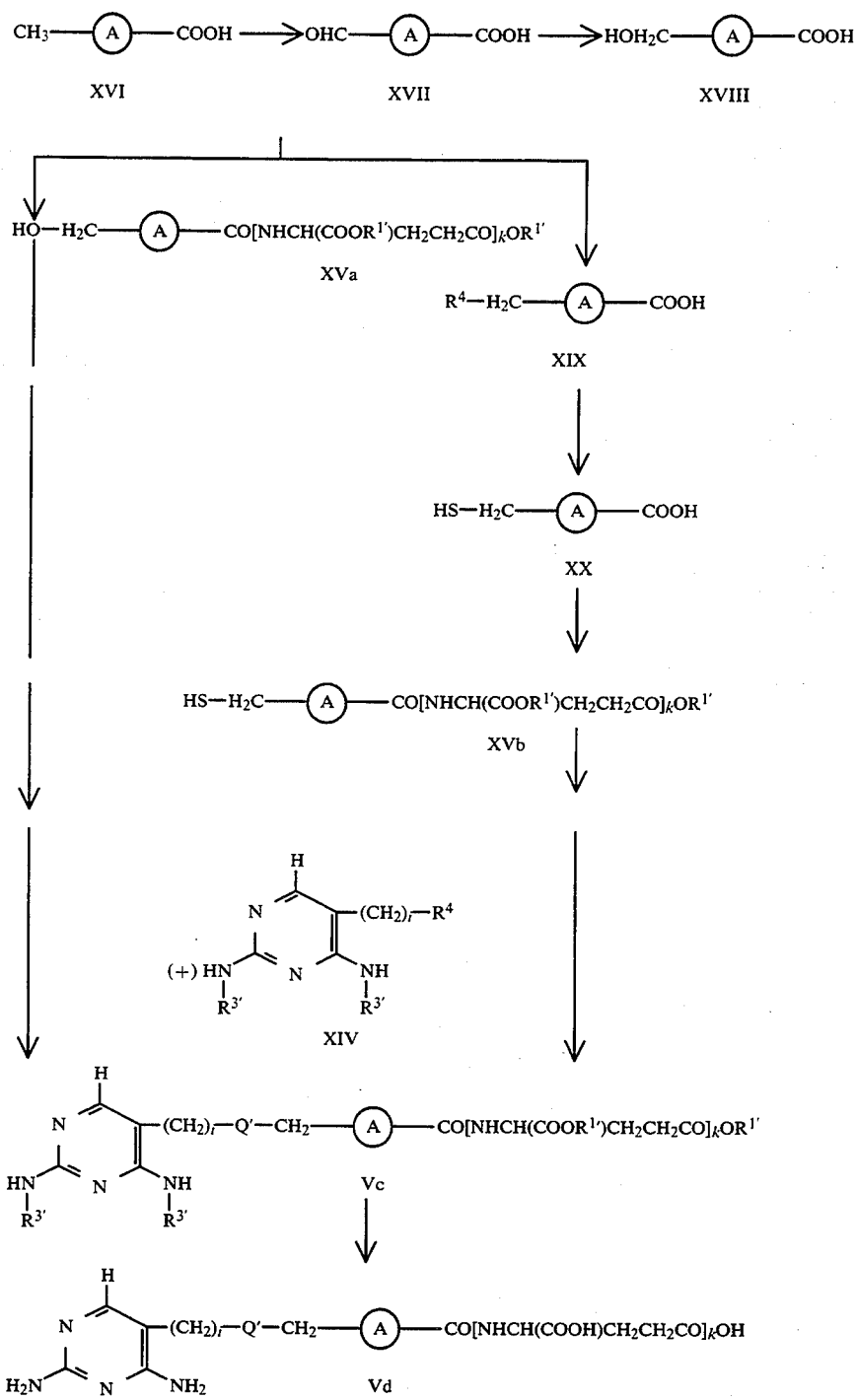

wherein $R^{1'}$, $R^{3'}$, $R^4$, i, $Q'$, (A) and k are as defined above.

Formula XVII compounds are prepared via standard oxidation of a formula xVI compound using oxidizing reagents such as, for example, potassium permanganate or chromium trioxide in the presence of acetic anhydride. The resulting formula XVII compound is then reduced to the corresponding alcohol (formula XVIII compounds).

At this stage in the present process, one option provides for the condensation of a formula XVIII compound with a glutamic acid derivative of formula IV, providing a hydroxymethylaryl glutamic acid derivative of formula XVa.

Alternatively, the alcohol functionality of a hydroxymethylbenzoic acid of formula XVIII is substituted with a leaving group via the above-described process depicted in Scheme IV. Preferred leaving groups for this aspect of the present process also are methanesulfonate and bromine. The resulting compound (formula XIX) is then thiolated (as shown in formula XX) or sulfonated via standard procedures.

Following the coupling of compounds of formula XX with a glutamic acid derivative of formula IV (formula XVb), compounds of either formulae XVa or XVb are condensed with a formula XIV compound, via procedures which are well known by one of ordinary skill in the art, giving novel intermediates of formula Vc. Final, pharmaceutically active compounds of formula Vd, which also are novel and useful for inhibiting DHFR and treating susceptible neoplasms in mammals, are prepared by deprotection of compounds of formula Vc via basic or acid hydrolysis.

The pharmaceutically acceptable salts of the invention are typically formed by reacting a compound of this invention which possesses one or more suitable acidic or basic functionalities with an equimolar excess amount of base or acid. The reactants generally are combined in a mutual solvent such as diethyl ether or benzene for acid addition salts, or water or alcohols for base addition salts. The salt usually precipitates out of solution within about 1 hour to about 10 days, and can be isolated by filtration or other conventional means.

In addition, some of the compounds of the present invention may form solvates with water or common organic solvents. Such solvates are included as compounds of this invention.

The compounds of this invention have an inhibitory effect on one or more enzyme (e.g. DHFR) which use folate as a substrate. For example, the following representative compounds have demonstrated inhibitory effects against growth of human T-cell derived lyphoblastic leukemia cells (CCRP-CEH):

N-{[4-(2,6-diamino-4-chloro-5-pyrimidinyl)propyl]-benzoyl-L-glutamic acid
N-{[4-(2,6-diamino-4-hydrogen-5-pyrimidinyl)ethyl]-benzoyl-L-glutamic acid
N-{[4-(2,6-diamino-4-hydrogen-5-pyrimidinyl)propyl]-benzoyl-L-glutamic acid
N-{[4-(2,6-diamino-4-hydrogen-5-pyrimidinyl)butyl]-benzoyl-L-glutamic acid
N-{[4-aminomethyl-2,6-diamino-4-hydrogen-5-pyrimidinyl)methyl]}benzoyl-L-glutamic acid
N-{4-[(2-amino-4-hydrogen-6-methyl-5-pyrimidinyl)-butyl]benzoyl}-L-glutamic acid The compounds of the present invention are antineoplastic agents and another preferred embodiment of the present invention provides a method of treating susceptible neoplasms in mammals, particularly humans, in need of such treatment. The present compounds are useful in inhibiting the growth of neoplasms such as, for example, choriocarcinoma, leukemia, adenocarcinoma of the female breast, epidermid cancers of the head and neck, squamous or small-cell lung cancer, various lymphosarcomas, and the like.

The instant compounds can be administered orally or parenterally, individually or in combination, preferably parenterally, and usually in the form of a pharmaceutical composition. Parenteral routes of administration include intramuscular, intrathecal, intravenous and intra-arterial. Oral dosage forms, including tablets and capsules, contain from 1 to 100 mg. of drug per unit dosage. Isotonic saline solutions containing 1–100 mg/mL can be used for parenteral administration.

Compositions are prepared in a manner well known in the pharmaceutical art and comprise at least one active compound. Accordingly, the present invention also includes pharmaceutical compositions comprising as active ingredient a compound of formula I or formula V, in which each $R^1$ is H, associated with at least one pharmaceutically acceptable carrier, diluent or excipient.

In making the compositions of the present invention, as well as compositions containing other compounds of formula I or formula V, the active ingredients are usually mixed with an excipient, diluted by an excipient or enclosed within such a carrier which can be in the form of a capsule, sachet, paper or other container. When the excipient serves as a diluent, it may be a solid, semi-solid or liquid material which acts as a vehicle, carrier or medium for the active ingredient. Thus, the compositions can be in the form of tablets, pills, powders, elixirs, suspensions, emulsions, solutions, syrups, soft and hard gelatin capsules, suppositories, sterile injectable solutions and sterile packaged powders.

In preparing a formulation it may be necessary to mill the active compound to provide the appropriate particle size prior to combining with the other ingredients. If the active compound is substantially insoluble, it ordinarily is milled to particle size of less than about 200 mesh. If the active compound is substantially water soluble, the particle size is normally adjusted by milling to provide a substantially uniform distribution in the formulation, e.g., about 40 mesh.

Some examples of suitable excipients include lactose, dextrose, sucrose, sorbitol, mannitol, starches, gum aracia, calcium silicate, microcrystalline cellulose, polyvinylpyrrolidone, cellulose, water, syrup, and methyl cellulose, the formulations can additionally include lubricating agents such as talc, magnesium stearate and mineral oil, wetting agents, emulsifying and suspending agents, preserving agents such as methyl- and propylhydroxybenzoates, sweetening agents or flavoring agents. The compositions of the invention can be formulated so as to provide quick, sustained or delayed release of the active ingredient after administration to the patient by employing procedures well known in the art.

The compositions are preferably formulated in a unit dosage form with each dosage normally containing from about 5 mg to about 1 g, more usually about 25 to about 800 mg. of the active ingredient. The term "unit dosage form" refers to physically discrete units suitable as unitary dosages for human subjects and other mammals, each unit containing a predetermined quantity of active material calculated to produce the desired therapeutic effect in association with a suitable pharmaceutical excipient.

The following formulation examples are illustrative only and are not intended to limit the scope of the invention in any way.

Formulation 1

Hard gelatin capsules are prepared using the following ingredients:

|  | Quantity (mg/capsule) |
| --- | --- |
| Active ingredient | 250 |
| Starch, dried | 200 |
| Magnesium stearate | 10 |
| Total | 460 mg |

Formulation 2

A tablet is prepared using the ingredients below:

|  | Quantity (mg/capsule) |
|---|---|
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3

An aerosol solution is prepared containing the following components:

|  | Percent |
|---|---|
| Active ingredient | 0.25 |
| Ethanol | 25.75 |
| Propellant 22 (Chlorodifluoromethane) | 70.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4

Tablets, each containing 60 mg of active ingredient, are made as follows:

|  | Quantity (mg/tablet) |
|---|---|
| Active ingredient | 60 |
| Starch | 45 |
| Microcrystalline cellulose | 35 |
| Polyvinylpyrrolidone (as 10% solution in water) | 4 |
| Sodium carboxymethyl starch | 4.5 |
| Magnesium stearate | 0.5 |
| Talc | 1 |
| Total | 150 |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. Sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of active ingredient, are made as follows:

|  | Quantity (mg/capsule) |
|---|---|
| Active ingredient | 80 |
| Starch | 59 |
| Microcrystalline cellulose | 59 |
| Magnesium stearate | 2 |
| Total | 200 |

The active ingredient, cellulose, starch, and magnesium stearate are blended, passed through a No. 45 mesh U.S. sieve, and filled into hard gelatin capsules in 200 mg quantities.

Formulation 6

Suppositories, each containing 225 mg of active ingredient, are made as follows:

|  | Quantity (mg/unit) |
|---|---|
| Active ingredient | 225 |
| Saturated fatty acid glycerides | 2,000 |
| Total | 2,225 |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of active ingredient per 5 mL dose, are made as follows:

|  | Quantity |
|---|---|
| Active ingredient(s) | 50 mg |
| Sodium carboxymethyl cellulose | 50 mg |
| Syrup | 1.25 mL |
| Benzoic acid solution | 0.10 mL |
| Flavor | q.v. |
| Color | q.v. |
| Purified water to total | 5 mL |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

|  | Quantity |
|---|---|
| Active ingredient | 100 mg |
| Isotonic saline | 1,000 mL |

Compounds of formulae I and V are effective against DHFR and susceptible neoplasms over a wide dosage range. For example, daily dosages will normally fall within the range of about 0.1 mg/kg to about 50 mg/kg of body weight. In the treatment of adult humans, the dosage range from about 5 mg/kg to about 25 mg/kg, in single or divided doses, is preferred. However, it will be understood that the amount of the compound actually administered, and the frequency of administration, will be determined by a physician in light of the relevant circumstances including the relative severity of a disease state, the choice of compound to be administered, the age, weight, and response of the individual patient, and the chosen route of administration. Therefore, the above dosage ranges are not intended to limit the scope of this invention in any way.

The following examples are provided to further illustrate the present invention. It is not intended that the invention be limited in scope by reason of any of the following examples.

Example 1

A. Preparation of methyl 4-(3-hydroxypropynyl)benzoate

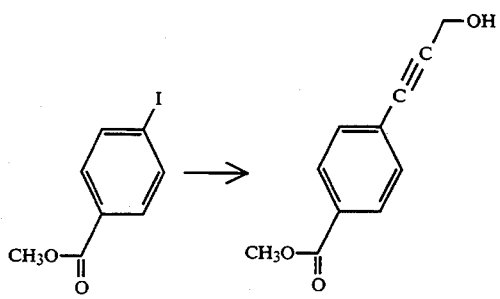

In a 1-L round bottom flask under a nitrogen atmosphere were charged 26.2 g (0.1 mol) of methyl p-iodobenzoate, 6.1 mL (0.105 mol) of 2-propyn-1-ol, 0.085 g (0.50 mmol) of palladium chloride, 0.26 g (1.0 mmol) of triphenylphosphine, and 0.19 g (1.0 mmol) of copper (I) iodide dissolved in 250 mL of diethylamine. The reaction mixture was stirred at ambient temperature for 20 hours. The volatiles were removed in vacuo, and the crude residue was thoroughly triturated in 700 mL of ether. The inorganic salt was filtered away, and the filtrate was concentrated in vacuo. The crude solid was then flash chromatographed on silica gel eluting with a gradient of 100% MeCl$_2$ to 25:75 EtOAc/MeCl$_2$. The correct fractions were combined and this dark solution was decolorized with animal charcoal powder. The charcoal was then filtered away, and the filtrate was removed in vacuo to give 18.0 g (95%) of methyl 4-(3-hydroxypropynyl)benzoate as a pale yellow solid.

R$_f$=0.46 (1:1 Hexane/EtOAc)
m.p.=88°-90° C.
Mass (FD) M+ =190
IR (KBr, cm°)=694, 771, 862, 996, 1015, 1028, 1118, 1172, 1191, 1277, 1309, 1406, 1430, 1449, 1606, 1724, 3379 UV (EtOH) λ$_{max}$=265, 203 (ε=25179, 16144) Anal. Calcd. for C$_{11}$H$_{10}$O$_3$: C, 69.46; H, 5.30. Found: C, 69.73; H, 5.39.
$^1$H NMR (300 MHz, CDCl$_3$) δ 1.76 (t, J=6.2 Hz, 1H), 3.94 (s, 3H) , 4.54 (d, J=6.2 Hz, 2H) , 7.51 (d, J=8.2 Hz, 2H) , 8.00 (d, J=8.3 Hz, 2H)

B. Preparation of methyl 4-(3-hydroxypropyl)benzoate

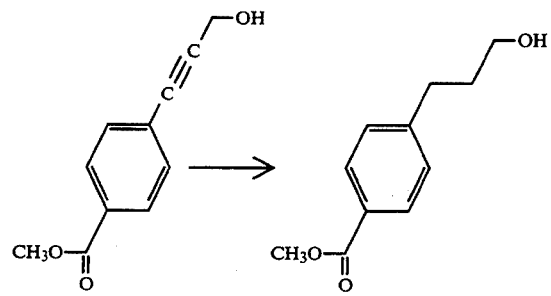

To a 2-L stainless steel Parr bottle was charged 17.1 g (89.9 mmol) of methyl 4-(3-hydroxypropynyl)benzoate dissolved in 1 L MeOH, followed by the addition of 2.6 g of 5% Pd/C catalyst. This mixture was then hydrogenated at ambient temperature for 18 hours on a Parr shaker at 15 psi of hydrogen gas. The catalyst was filtered away, and washed with fresh MeOH. The filtrate was removed in vacuo, and the crude residue was flash chromatographed on silica gel eluting with 25% EtOAc/MeCl$_2$. The correct fractions were combined and the solvents were removed in vacuo to give 16.7 g (95%) of methyl 4-(3-hydroxypropyl)benzoate as a colorless oil.

R$_f$=0.36 (25% EtOAc/MeCl$_2$)
Mass (FD) M+ =194
IR (KBr, cm$^{-1}$)=1020, 1046, 1114, 1181, 1194, 1247, 1312, 1416, 1437, 1611, 1718, 2953, 3011, 3026, 3626 UV (EtOH) λ$_{max}$=265, 203 (ε=25179, 16144) Anal. Calcd. for C$_{11}$H$_{14}$O$_3$: C, 68.02; H, 7.27. Found: C, 67.95;H, 6.97.
$^1$H NMR (300 MHz, CDCl$_3$) δ1.32 (t, J=5.5 Hz, 1H), 1.88-197 (m, 2H), 2.79 (t, J=7.7 Hz, 2H), 3.70 (q, J=6.1 Hz, 2H), 3.92 (s, 3H), 7.29 (d, J=8.0 Hz, 2H), 7.98 (d, J=8.2 Hz, 2H)

C. Preparation of methyl 4-(3-methylsulfonyloxypropyl)benzoate

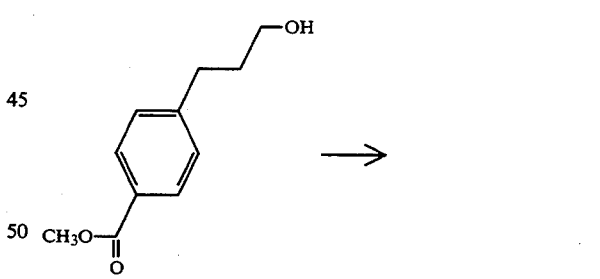

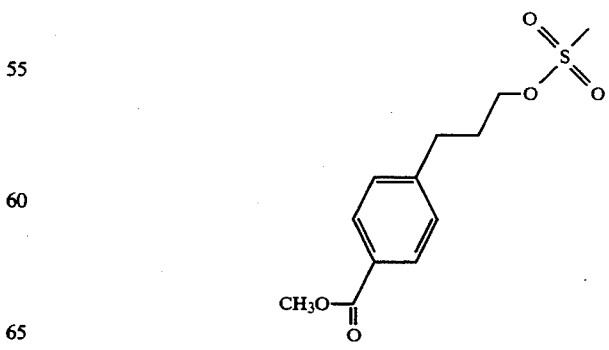

To a 250 mL flame-dried flask under a nitrogen atmosphere was charged 5.6 g (28.9 mmol) of methyl 4-(3- hydroxypropyl)benzoate dissolved in 70 mL of anhydrous ether, followed by the addition of 4.2 mL (30.3 mmol) of triethylamine. After cooling the stirring solution down in an ice bath, the reaction was treated slowly with 2.35 mL (30.3 mmol) of methanesulfonyl chloride. The ice bath was removed, and the the thick white mixture was stirred at ambient temperature for 18 hours. The reaction was then diluted with some additional ether and washed with water, dried over $Na_2SO_4$, and removed in vacuo. The solid was triturated in hexanes and filtered to give 7.35 g (93%) of methyl 4-(3-methylsulfonyloxypropyl)benzoate as a fluffy white solid.

$R_f$=0.37 (1:1 EtOAc/Hex)
m.p.=57°-58° C.

Mass (FAB) M+1 HRMS=Calcd.: 273.0796; Found: 273.0787

IR (KBr, $cm^{-1}$)=518, 531, 544, 709, 765, 841, 925, 973, 1005, 1108, 1170, 1282, 1333, 1353, 1366, 1713 UV (EtOH) $\lambda_{max}$=239, 203 ($\epsilon$=16524, 19500)

$^1$H NMR (300 MHz, $CDCl_3$) δ2.09-2.14 (m, 2H), 2.84 (t, J=7.6 Hz, 2H), 3.02 (s, 3H), 3.93 (s, 3H), 4.25 (t, J=6.2 Hz, 2H), 7.29 (d, J=8.1, 2H), 8.00 (d, J=8.2 Hz, 2H)

D. Preparation of 4-[2,4-diamino-1,6-dihydroxy-6-oxo-5-pyrimidinyl)propyl]benzoate

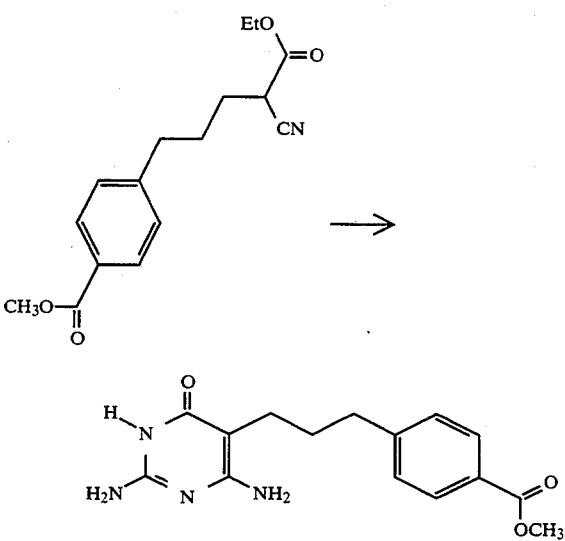

To a 100 mL 2-neck round bottom flask flame dried under an Argon atmosphere was charged 0.75 g (7.9 mmol) of guanidine hydrochloride dissolved in freshly distilled t-butanol. To this solution was added portionwise at ambient temperature. 0.18 g (7.9 mmol) of sodium metal. This mixture was then heated to 60° C. for 2.5 hours. Next, 1.63 g (5.63 mmol) of methyl 4-(4-cyano-4-ethoxycarbonylbutyl)benzoate was added and the reaction mixture was heated to 85° C. for 2.5 hours. The volatiles were removed in vacuo, and this residue was triturated in 50 mL of ice water and the pH was adjusted quickly from 11 to 3 using 5N HCl. The solid was filtered and dried in a vacuum oven. Finally, the solid was triturated in 20 mL of ether, filtered and dried to give 0.76 g (45%) of methyl 4-[2,4-diamino-1,6-dihydroxy-6-oxo-5-pyrimidinyl)propyl]benzoate as an off-white solid.

$R_f$=0.44 (20% MeOH/CHCl$_3$)
m.p.=159°-162° C. (dec)

Mass (FAB) M+1 HRMS=Calcd.: 303.1457; Found: 303.1464

IR (KBr, $cm^{-1}$)=560, 705, 764, 1020, 1113, 1179, 1286, 1370, 1435, 1610, 1718, 3176 UV (EtOH) $\lambda_{max}$=353,274, 239, 205 ($\epsilon$=4450, 11483, 19129, 24889)

$^1$H NMR (300 MHz, DMSO$_{d6}$) δ1.54-1.80 (m, 3H), 2.22 (t, J=7.4 Hz, 1H), 2.61 (t, J=7.9 Hz, 2H), 3.80 (s, 3H), 5.93 (br s, 2H), 6.26 (br s, 2H), 7.34 (d, J=8.9 Hz, 2H), 7.87 (d, J=8.4 Hz, 2H)

E. Preparation of methyl 4-(4-cyano-4-ethoxycarbonylbutyl)benzoate

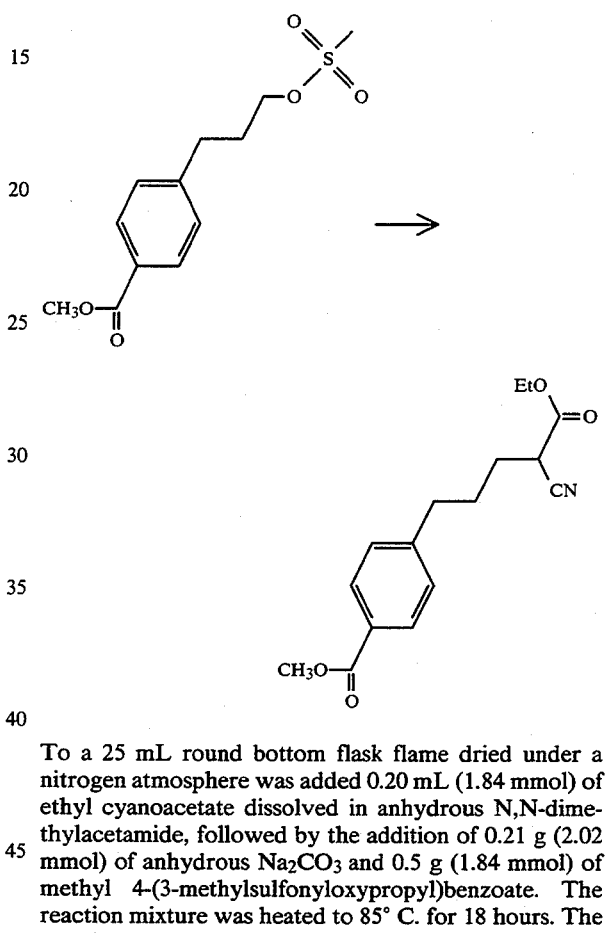

To a 25 mL round bottom flask flame dried under a nitrogen atmosphere was added 0.20 mL (1.84 mmol) of ethyl cyanoacetate dissolved in anhydrous N,N-dimethylacetamide, followed by the addition of 0.21 g (2.02 mmol) of anhydrous $Na_2CO_3$ and 0.5 g (1.84 mmol) of methyl 4-(3-methylsulfonyloxypropyl)benzoate. The reaction mixture was heated to 85° C. for 18 hours. The reaction turned a light red color. After cooling to ambient temperature, the reaction mixture was poured into 500 mL of ether and water. The aqueous layer was washed again with fresh ether. The ether layers were combined, dried over $Na_2SO_4$, and removed in vacuo to give a crude red oil. This residue was then flash chromatographed on silica gel eluting with 2:1 Hexane/EtOAc. The pure fractions were combined and removed in vacuo to give 0.17 g (32%) of methyl 4-(4-cyano-4-ethoxycarbonylbutyl)benzoate as a pale yellow oil.

$R_f$=0.31 (1:1 EtOAc/Hex)
Mass (FD) M+=289

IR (KBr, $cm^{-1}$)=1020, 1114, 1181, 1230, 1311, 1371, 1416, 1437, 1612, 1719, 1747, 2954, 3027 UV (EtOH) $\lambda_{max}$ =238, 203 ($\epsilon$=19400, 22519) Anal. Calcd. for $C_{16}H_{19}NO_4$: C, 66.42; H, 6.62; N, 4.84. Found: C, 66.62; H, 6.49; N, 4.87.

$^1$H NMR (300 MHz, CDCl$_3$) δ1.30 (t, J=7.1 Hz, 3H), 1.87-2.01 (m, 4H), 2.76 (t, J=7.0 Hz, 2H), 3.49 (t, J=6.8

Hz, 3H), 3.93 (s, 3H), 4.27 (q, J=7.1 Hz, 2H), 7.26 (d, J=8.3 Hz, 2H), 7.99 (d, J=8.2 Hz, 2H)

F. Preparation of methyl-(4-cyano-4-ethoxycarbonylbutyl)benzoate

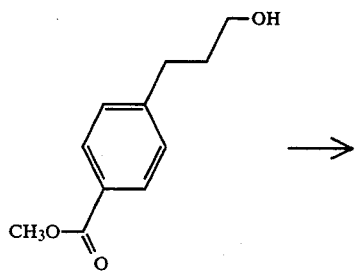

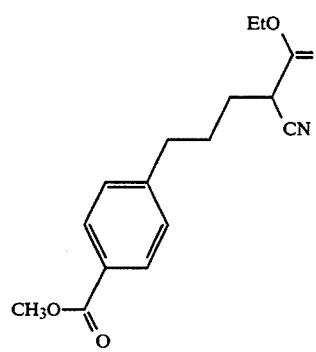

To a 250 mL flame dried round bottom flask were charged 10.0 g (51.5 mmol) of methyl 4-(-hydroxypropyl)benzoate and 5.48 mL (51.5 mmol) of ethyl cyanoacetate dissolved in 40 mL of anhydrous tetrahydrofuran (THF). To this solution was then added dropwise to a solution of 20.2 g (77 mmol) of triphenylphosphine and 12.1 mL (77 mmol) of diethyl azodicarboxylate dissolved in 60 mL of anhydrous THF. After the addition, the reaction was stirred at ambient temperature for 1.5 hours. The volatiles were removed in vacuo and the crude oil was dissolved in 300 mL of EtOAc, washed with brine, dried over Na2SO4, and removed in vacuo. This crude oil was then purified on silica gel using a Waters Prep LC 2000 eluting with a gradient of 1:1 MeCl2/Hex to 100% MeCl2 to give 6.0 g (40%) of methyl 4-(4-cyano-4-ethoxycarbonylbutyl)benzoate as a pale yellow oil.

R$_f$=0.31 (1:1) EtOAc/Hex)

Mass (FD) M+ =289

IR (KBr, cm$^{-1}$)=1020, 1114, 1181, 1230, 1311, 1371, 1416, 1437, 1612, 1719, 1747, 2954, 3027 UV (EtOH) $\lambda_{max}$=238, 203 ($\epsilon$=19400, 22519) Anal. Calcd. for C$_{16}$H$_{19}$NO$_4$: C, 66.42; H, 6.62; N, 4.84. Found: C, 66.62; H, 6.49; N, 4.87.

$^1$H NMR (300 MHz, CDCl$_3$) δ1.30 (t, J=7.1 Hz, 3H), 1.87-2.01 (m, 4H), 2.76 (t, J=7.0 Hz, 2H), 3.49 (t, J=6.8 Hz, 3H), 3.93 (s, 3H), 4.27 (q, J=7.1 Hz, 2H), 7.26 (d, J=8.3 Hz, 2H), 7.99 (d, J=8.2 Hz, 2H)

G. Preparation of 4-[2,4-diamino-1,6-dihydroxy-6-oxo-5-pyrimidinyl)propyl]benzoic acid

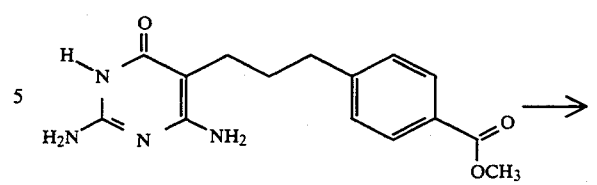

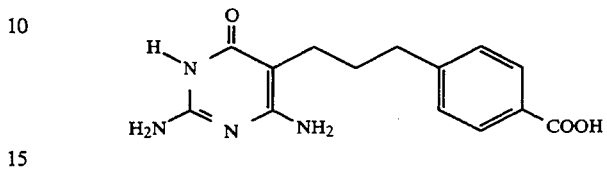

To a 100 mL round bottom flask was charged 0.75 g (2.48 mmol) of methyl 4-[2,4-diamino-1,6-dihydroxy-6-oxo-5-pyrimidinyl)propyl]benzoate in 30 mL of 1N NaOH. The mixture was heated to 50° C. for 1.5 hours. The yellow solution was then cooled down in an ice bath and acidified to pH 3 using 5N HCl. The precipitate was filtered, washed with cold water, and dried in a vacuum oven at 60° C. to give 0.60 g (84%) of 4-[2,4-diamino-1,6-dihydroxy-6-oxo-5-pyrimidinyl)propyl]benzoic acid as an off-white solid.

R$_f$=0.35 (50% MeOH/CHCl$_3$)

m.p.=275°-278° C. (dec)

Mass (FAB) M+1 HRMS=Calcd.: 289. 1300 Found: 289.1304

IR (KBr, cm$^{-1}$) 546, 755, 1019, 1177, 1265, 1376, 1446, 1611, 3381 UV (EtOH) $\lambda_{max}$=276, 239, 206 ($\epsilon$=13095, 19385, 26064)

$^1$H NMR (300 MHz, DMSO$_{d6}$) δ1.51-1.80 (m, 3H), 2.21 (t, J=7.4 Hz, 1H), 2.58-2.71 (m, 2H), 5.70 (s, 2H), 5.93 (s, 2H), 7.28 (d, J=8.3 Hz, 2H), 7.85 (d, J=8.4 Hz, 2H), 9.80 (br s, 1H), 12.70 (br s, 1H)

H. 4-[(2,6-diamino-4-chloro-5-pyrimidinyl)propyl]benzoic acid

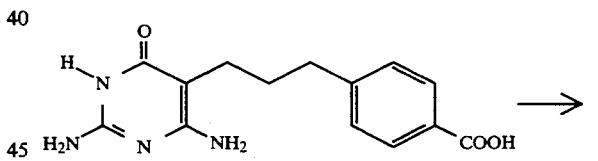

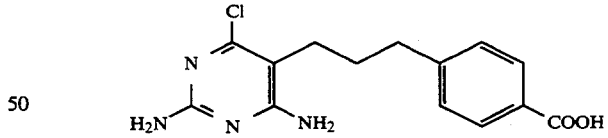

To a 50 mL round bottom flask were charged 0.59 g (2.05 mmol) of 4-[2,4-diamino-1,6-dihydroxy-6-oxo-5-pyrimidinyl)propyl]benzoic acid, and 0.26 mL (2.05 mmol) of N,N-dimethylaniline in 7 mL of phosphorus oxychloride. The mixture was heated to 90° C. for 5 hours. The dark solution was cooled to ambient temperature and the volatiles were removed in vacuo to near dryness. This residue was diluted with a small amount of ether and poured into an Erlenmeyer containing 200 mL of 5% NaHCO$_3$. The pH was adjusted to 2 using 5N HCl. The solid was triturated in the acidic water, filtered, and dried in a vacuum oven at 50° C. The solid was then triturated in 50 mL of ether, filtered, and dried to give 0.56 g (89%) of 4-[(2,6-diamino-4-chloro-5-pyrimidinyl)propyl]benzoic acid as a pale yellow solid.

R$_f$=0.66 (20% MeOH/CHCl$_3$)

m.p.=>300° C. (dec)

Mass (FAB) M+1 HRMS=Calcd.: 307.0962; Found: 307.0951

IR (KBr, cm$^{-1}$)=542, 1058, 1175, 1222, 1417, 1610, 3184 UV (EtOH) $\lambda_{max}$=281, 240, 206 ($\epsilon$=5386, 15926, 16048)

$^1$H NMR (300 MHz, DMSO$_{d6}$) $\delta$1.62-1.77 (m, 3H), 2.60-2.72 (m, 3H), 7.35 (d, J=8.0 Hz, 2H), 7.85 (d, J=8.0 Hz, 2H)

I. N-{[4-(2,6-diamino -4-chloro-5-pyrimidinyl)propyl]-benzoyl}-L-glutamic acid diethyl ester

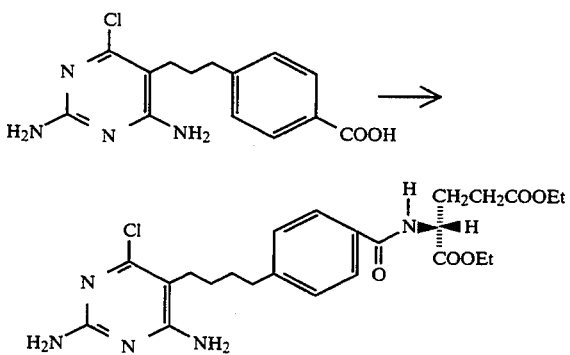

To a 50 mL flame dried round bottom flask under a nitrogen atmosphere was charged 0.55 g (1.79 mmol) of 4-[(2,6-diamino-4-chloro-5-pyrimidinyl)propyl]benzoic acid dissolved in 15 mL of anhydrous DMF, followed by the addition of 0.32 g (2.06 mmol) of 2-chloro-4,6-dimethoxy-1,3,5-triazine and 0.20 mL (1.79 mmol) of 4-methylmorpholine. The pale yellow solution was stirred at ambient temperature for 30 minutes. Next, 0.43 g (1.79 mmol) of L-glutamic acid diethyl ester hydrochloride was added along with 0.20 mL (2.06 mmol) of 4-methylmorpholine. The reaction mixture was then stirred at ambient temperature for 2 hours. The volatiles were removed in vacuo, and the crude residue was dissolved in CHCl$_3$, washed with brine, dried over Na$_2$SO$_4$, and removed in vacuo. The crude residue was then flash chromatographed on silica gel eluting with 3% MeOH/EtOAc. The correct fractions were combined to give 0.15 g (17%) of N-{[4-(2,6-diamino-4-chloro-5-pyrimidinyl)propyl]benzoyl}-L-glutamic acid diethyl ester as a pale yellow solid.

R$_f$=0.40 (4% MeOH/EtOAc)

m.p.=72°-75° C.

Mass (FAB) M+1 HRMS=Calcd.: 492.2013; Found: 492.1985

IR (KBr, cm$^{-1}$)=885, 1020, 1205, 1456, 1540, 1624, 1736, 3364 UV (EtOH) $\lambda_{max}$=289, 238, 207 ($\epsilon$=7611, 22480, 23467)

$^1$H NMR (300 MHz, DMSO$_{d6}$) $\delta$1.11-1.23 (m, 7H), 1.64-1.67 (m, 2H), 1.97-2.09 (m, 2H), 2.41 (t, J=7.4 Hz, 4H), 2.67 (t, J=7.7 Hz, 2H), 3.99-4.11 (m, 4H), 4.36-4.44 (m, 1H), 6.04 (s, 2H), 6.50 (s, 2H), 7.28 (d, J=8.1 Hz, 2H), 7.78 (d, J=8.1 Hz, 2H), 8.62 (d, J=7.4 Hz, 1H)

J. Preparation of N-{[4-(2,6-diamino-5-pyrimidinyl)propyl]benzoyl}-L-glutamic acid diethyl ester

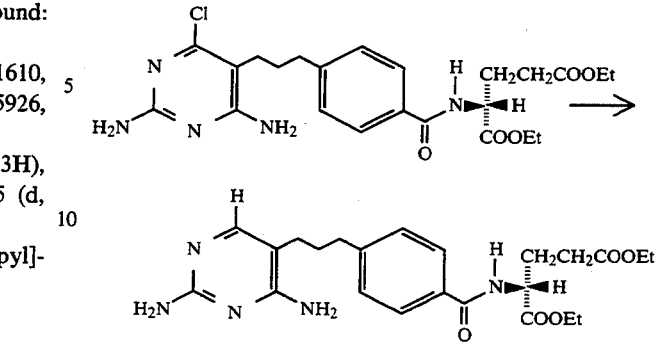

To a 50 mL round bottom flask was charged 0.14 g (0.28 mmol) of N-{[4-(2,6-diamino-4-chloro-5-pyrimidinyl)-propyl]benzoyl)-L-glutamic acid diethyl ester dissolved in 15 mL of absolute ethanol, followed by the addition of 0.10 g of 10% Pd/C catalyst. This mixture was then hydrogenated at 60 psi of hydrogen gas on a Parr shaker at 50° C. for 1 hour. The catalyst was filtered, washed with fresh ethanol, and the filtrate was removed in vacuo. The crude residue was then flash chromatographed on silica gel eluting with 10% MeOH/CHCl$_3$. The correct fractions were collected and removed in vacuo to give 0.042 g (33%) of N-{[4-(2,6-diamino-5-pyrimidinyl)propyl]benzoyl}-L-glutamic acid diethyl ester as a white solid.

R$_f$=0.15 (10% MeOH/CHCl$_3$)

m.p.=95°-98° C.

Mass (FAB) M+1 HRMS=Calcd.: 458.2403; Found: 458.2402

IR (KBr, cm$^{-1}$) 1186, 1463, 1564, 1621, 1735 UV (EtOH) $\lambda_{max}$=289, 237,206 ($\epsilon$=4086, 14528, 15380)

$^1$H NMR (300 MHz, DMSO$_{d6}$) $\delta$1.11-1.26 (m, 7H), 1.61-1.75 (m, 2H), 1.95-2.09 (m, 2H), 2.27 (t, J=7.4 Hz, 2H), 2.41 (t, J=7.2 Hz, 1H), 2.62 (t, J=7.7 Hz, 2H), 3.99-4.11 (m, 2H), 4.36-4.44 (m, 1H), 5.63 (s, 2H), 6.15 (s, 2H), 7.28 (d, J=8.1 Hz, 2H), 7.45 (s, 1H), 7.78 (d, J=8.1 Hz, 2H), 8.62 (d, J=7.4 Hz, 1H )

K. Preparation of N-{[4-(2,6-diamino-5-pyrimidinyl)-propyl]benzoyl}-L-glutamic acid

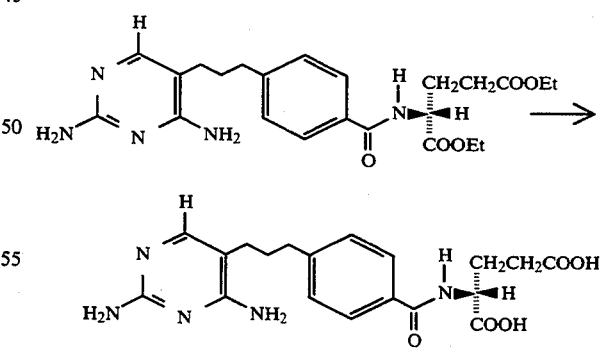

To a 15 mL round bottom flask was charged 0.034 g (0.074 mmol) of N-{[4-(2,6-diamino-5-pyrimidinyl)-propyl]benzoyl}-L-glutamic acid diethyl ester dissolved in 2 mL of 1N NaOH and 1 mL of methanol. The colorless solution was stirred at ambient temperature for 4 hours. The volatiles were removed in vacuo to near dryness and this residue was treated with a small amount of water. The pH was carefully adjusted to 3 using 1N HCl , and the precipitate formed was cooled down in an ice bath. The solid was then filtered, washed with cold water, and dried in a vacuum oven at 60° C. to give 0.016 g (54%) of N-{[4-(2,6-diamino-5-pyrimidinyl)propyl]benzoyl}-L-glutamic acid as a white solid.

$R_f$=0.04 (50% MeOH/CHCl$_3$)
m.p.=191°-19° C. (dec)
Mass (FAB) M+1 HRMS=Calcd.: 402.1777; Found: 402.1790
IR (KBr, cm$^{-1}$)=589, 1501, 1663, 3359 UV (EtOH) $\lambda_{max}$32 286, 236, 201 ($\epsilon$=6384, 20551, 1306)
$^1$H NMR (300 MHz, DMSO$_{d6}$) δ1.67–1.76 (m, 2H), 1.88–2.24 (m, 2H), 2.30 (d, J=5.9 Hz, 4H) , 2.63 (t, J=7.3 Hz, 2H), 4.30–4.37 (m, 1H), 6.41 (s, 2H), 6.76 (s, 2H), 7.28 (d, J=8.0 Hz, 2H), 7.46 (s, 1H), 7.77 (d, J=8.0 Hz, 2H), 8.39 (d, J=7.6 Hz, 1H)

L. Preparation of N-{[4-(2,6-diamino-4-chloro-5-pyrimidinyl)propyl]benzoyl}-L-glutamic acid di-t-butyl ester pyrimidinyl)propyl]benzoyl}-L-glutamic acid di-t-butyl ester as a white solid.

$R_f$=0.48 (4% MeOH/EtOAc)
m.p.=110°-112° C.
Mass (FAB) M+=548
IR (KBr, cm$^{-1}$)=754, 795, 847, 888, 1152, 1259, 1369, 1394, 1456, 1502, 1540, 1583, 1625, 1730, 2933, 2979, 3209, 3359 UV (EtOH) $\lambda_{max}$=289, 238, 203 ($\epsilon$=6901, 21921, 44982) Anal. Calcd. for C$_{27}$H$_{38}$N$_5$O$_5$Cl: C, 59.17; H, 6.99; N, 12.78. Found: C, 58.92; H, 7.14; N, 12.56.
$^1$H NMR (300 MHz, DMSO$_{d6}$) δ1.36 (s, 9H), 1.38 (s, 9H), 1.63–1.67 (m, 2H), 2.30 (t, J=7.4 Hz, 2H), 2.69 (t, J=7.6 Hz, 2H), 3.97–4.30 (m, 1H), 6.03 (s, 2H), 6.50 (s, 2H), 7.27 (d, J=8.0 Hz, 2H), 7.77 (d, J=8.0 Hz, 2H), 8.48 (d, J=7.6 Hz, 1H)

M. Preparation of N-{[4-(2,4-diamino-5-pyrimidinyl)propyl]benzoyl}-L-glutamic acid di-t-butyl ester

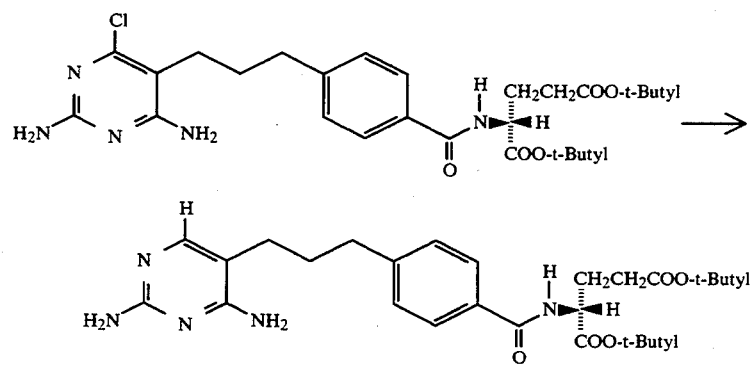

ester

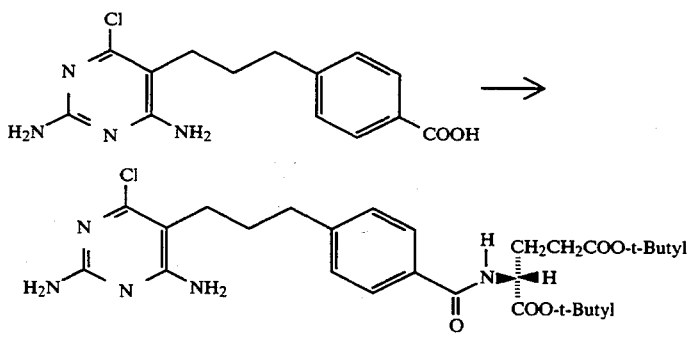

To a 250 mL 3-neck flame dried round bottom flask under an Argon atmosphere were charged 2.0 g (6.5 mmol) of 4-[(2,6-diamino-4-chloro-5-pyrimidinyl)propyl]benzoic acid dissolved in 60 mL of anhydrous DMF, followed by the addition of 1.14 g (6.5 mmol) of 2-chloro-4,6-dimethoxy-1,3,5-triazine and 0.72 mL (6.5 mmol) of 4-methylmorpholine. The pale yellow solution was stirred at ambient temperature for 30 minutes. Next, 1.93 g (6.5 mmol) of L-glutamic acid di-t-butyl ester hydrochloride were added along with 0.72 mL (6.5 mmol) of 4-methylmorpholine. The reaction mixture was then stirred at ambient temperature for 3 hours. The volatiles were removed in vacuo, and the crude residue was dissolved in CHCl$_3$, washed with brine, dried over NaSO$_4$, and concentrated in vacuo to a volume of 15 mL. This crude residue was then flash chromatographed on silica gel eluting with 100% EtOAc. The correct fractions were combined to give 0.97 g (27%) of N-{[4-(2,6-diamino-4-chloro-5-

To a 250 mL round bottom flask were charged 2.45 g (4.47 mmol) of N-{[4-(2,6-diamino-4-chloro-5-pyrimidinyl)propyl]benzoyl}-L-glutamic acid di-t-butyl ester dissolved in 150 mL of absolute ethanol, followed by the addition of 3.75 g of palladium black catalyst added in three equal portions. This stirring mixture was hydrogenated at ambient temperature under a balloon containing hydrogen gas for 24 hours. The catalyst was filtered, washed with fresh ethanol, and the filtrate was removed in vacuo. The crud residue was then dissolved in CHCl$_3$, washed with 5% NaHCO$_3$, dried over Na$_2$SO$_4$, and removed in vacuo. This crude residue was then flash chromatographed on silica gel eluting with 15% MeOH/CHCl$_3$. The correct fractions were collected and removed in vacuo to give 1.8 g (78%) of N-{[4-(2,4-diamino-5-pyrimidinyl)propyl]benzoyl}-L-glutamic acid di-t-butyl ester as an off-white solid.

$R_f$=0.50 (20% MeOH/CHCl$_3$)

m.p.=82°-85° C. (foam, dec)
Mass (FAB) M+1=514
IR (KBr, cm⁻¹)=597, 752, 803, 846, 1100, 1152, 1257, 1369, 1393, 1456, 1504, 1563, 1731, 2933, 2979, 3212, 3366 UV (EtOH) $\lambda_{max}$=290, 237, 202 ($\epsilon$=6182, 22346, 41959) Anal. Calcd. for $C_{27}H_{39}N_5O_5$: C, 63.14; H, 7.65; N, 13.64. Found: C, 62.93; H, 7.75; N, 13.56.

$^1$H NMR (300 MHz, DMSO$_{d6}$) $\delta$1.36 (s, 9H), 1.38 (s, 9H), 1.64–1.72 (m, 2H), 1.86–2.01 (m, 2H), 2.24–2.48 (m, 4H), 2.61 (t, J=7.7 Hz, 2H), 4.28–4.30 (m, 1H), 5.61 (s, 2H), 6.13 (s, 2H), 7.27 (d, J=7.5 Hz, 2H), 7.44 (s, 1H), 7.77 (d, J=7.4 Hz, 2H), 8.48 (d, J=7.4 Hz, 1H)

N. Preparation of N-{[4-(2,4-diamino-5-pyrimidinyl)propyl]benzoyl}-L-glutamic acid

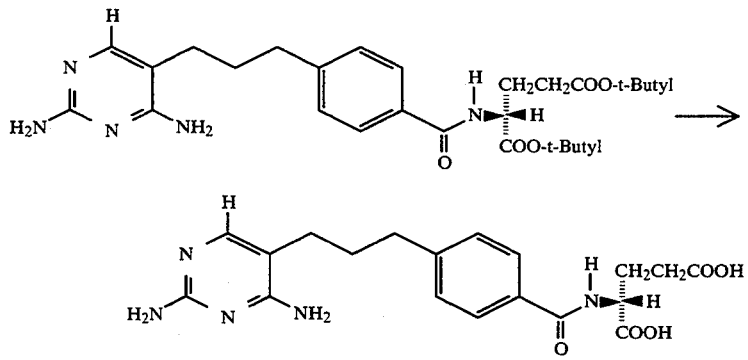

After flame drying a 100 mL round bottom flask, 2.0 g (3.89 mmol) of N-{[4-(2,4-diamino-5-pyrimidinyl)propyl]benzoyl}-L-glutamic acid di-t-butyl ester were dissolved in 40 mL of fresh trifluoroacetic acid (TFA) and stirred under an Argon atmosphere for 5 hours at ambient temperature. The TFA was removed in vacuo, and the residue was treated with ether. The white solid was filtered, washed with fresh ether, and dried in a vacuum overn at 60° C. to give 1.61 g (80%) of N-{[4-(2,4-diamino-5-pyrimidinyl)propyl]benzoyl}-L-glutamic acid as a white solid.

$R_f$=0.16 (50% MeOH/CHCl$_3$)
m.p.=136°-138° C. (foam)
Mass (FAB) M+1 HRMS=Calcd.: 402.179700; Found: 402.177744
IR (KBr, cm⁻¹)=1193, 1440, 1503, 1537, 1665, 3423
UV (EtOH) $\lambda_{max}$=234, 205 ($\epsilon$=21325, 35169)

$^1$H NMR (300 MHz, DMSO$_{d6}$) $\delta$1.11–1.26 (m, 7H), 1.61–1.75 (m, 2H), 1.95–2.09 (m, 2H), 2.27 (t, J=7.4 Hz, 2H), 2.41 (t, J=7.2 Hz, 1H), 2.62 (t, J=7.7 Hz, 2H), 3.99–4.11 (m, 2H), 4.36–4.44 (m, 1H), 5.63 (s, 2H), 6.15 (s, 2H), 7.28 (d, J=8.1 Hz, 2H), 7.45 (s, 1H), 7.78 (d, J=8.1 Hz, 2H), 8.62 (d, J=7.4 Hz, 1H)

O. Preparation of N-{[4-(2,6-diamino-4-chloro-5-pyrimidinyl)propyl]benzoyl}-L-glutamic acid

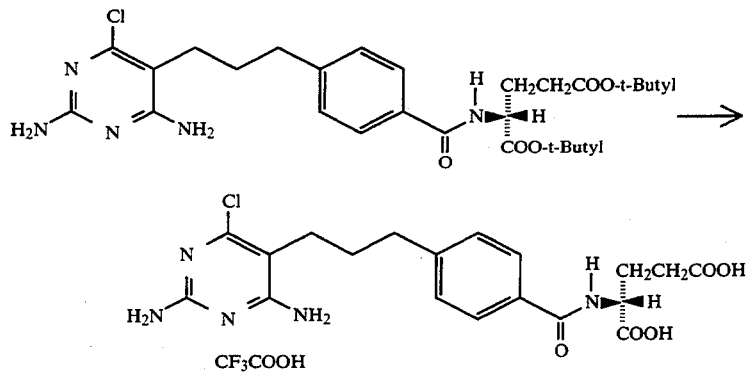

After flame drying a 15 mL round bottom flask, 0.040 g (0.073 mmol) of N-{[4-(2,6-diamino-4-chloro-5-pyrimidinyl)propyl]benzyl}-L-glutamic acid di-t-butyl ester were dissolved in 1 mL of fresh TFA and stirred under an Argon atmosphere for 3.5 hours at ambient temperature. The TFA was removed in vacuo, and the residue was treated with ether. The white solid was filtered, washed with fresh ether, and dried in a vacuum oven at 60° C. to give 0.029 g (72%) of N-{[4-(2,6-diamino-4-chloro-5-pyrimidinyl)propyl]benzoyl}-L-glutamic acid as a white solid.

$R_f$=0.16 (50% MeOH/CHCl$_3$)
m.p.=115°-118° C. (foam)
Mass (FAB) M+1 HRMS=Calcd.: 436.1291; Found: 436.1388
IR (KBr, cm⁻¹)=840, 1141, 1200, 1290, 1354, 1448, 1506, 1540, 1644, 3353 UV (EtOH) $\lambda_{max}$=289, 238, 203 ($\epsilon$=7817, 26481, 50610)

$^1$H NMR (300 MHz, DMSO$_{d6}$) $\delta$1.64–1.68 (m, 2H), 1.90–2.03 (m, 4H), 2.04–2.07 (m, 2H), 2.32 (t, J=7.1 Hz, 2H), 2.68 (t, J=7.4 Hz, 2H), 4.34–4.37 (m, 1H), 6.18 (brs, 2H), 7.27 (d, J=7.8 Hz, 2H), 7.78 (d, J=7.9 Hz, 2H), 8.50 (d, J=7.6 Hz, 1H)

Example 2

A. Preparation of 4-[(2,6-diamino-4-chloro-5-pyrimidinyl)butyl]benzoic acid

B. Preparation of N-{[4-(2,6-diamino-4-chloro-5-pyrimidinyl)butyl]benzoyl}-L-glutamic acid diethyl ester

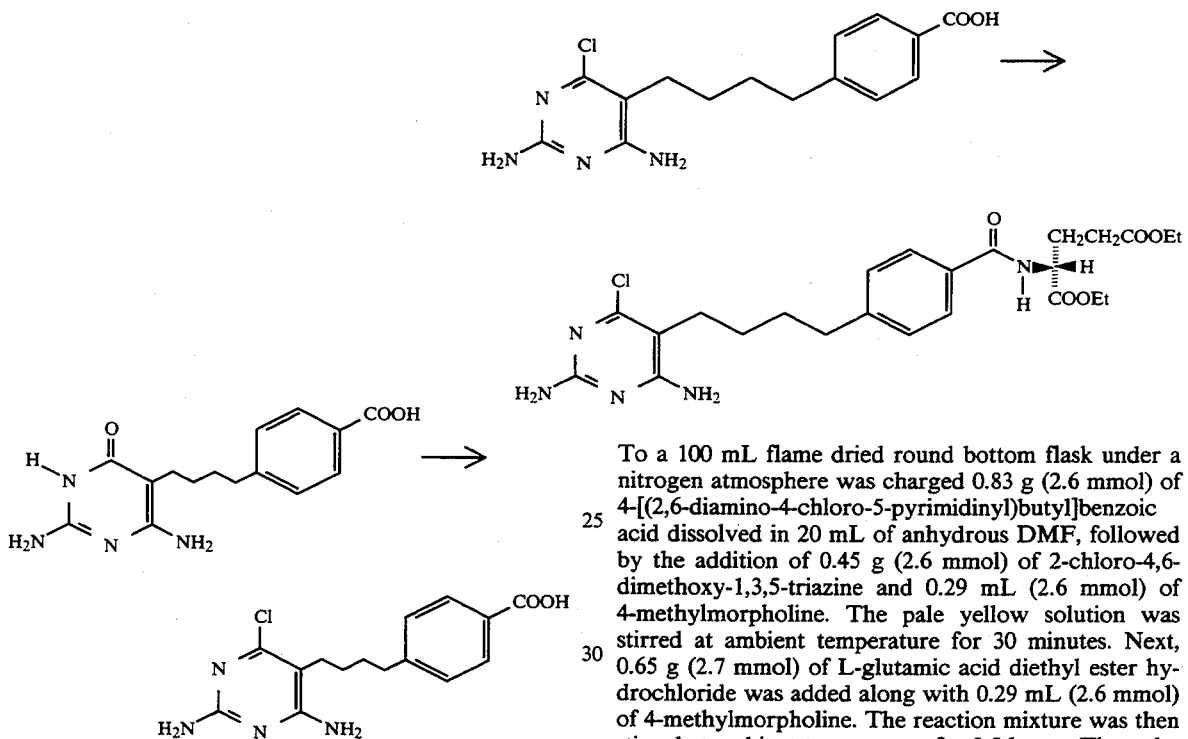

To a 25 mL round bottom flask flame dried under a nitrogen atmosphere was charged 0.5 g (1.7 mmol) of 4-[(2,4-diamino-1,6-dihydro-6-oxo-5-pyrimidinyl)-butyl]benzoic acid [as taught by Taylor, E. C., et al., Heterocycles, 28(2):1169-1178 (1989)] suspended in 5 mL of phosphorus oxychloride. The mixture was heated to reflux temperature for 5 hours. After cooling the solution to ambient temperature, the POCl₃ was removed in vacuo, and the residue was triturated in 50 mL of water, filtered, washed with fresh water, and dried in a vacuum oven at 60° C. to give 0.47 g (88%) of 4-[(2,6-diamino-4-chloro-5-pyrimidinyl)butyl]benzoic acid as an off-white solid.

$R_f$=0.66 (20% MeOH/CHCl₃)
m.p.=228°-231° C. (dec)
Mass (FAB) M+1 HRMS=Calcd.: 320.1166; Found: 320.1170
IR (KBr, cm⁻¹) 540, 765, 1018, 1073, 1177, 1244, 1417, 1508, 1610, 1655, 2933, 3183, 3343 UV (EtOH) $\lambda_{max}$=277, 240, 202 ($\epsilon$=5722, 15488, 25210)
¹H NMR (300 MHz, DMSO$_{d6}$) δ1.29-1.80 (m, 6H), 2.50-2.64 (m, 2H), 6.80 (br s, 2H), 7.25 (d, J=8.4 Hz, 2H), 7.40 (br s, 2H), 7.82 (d, J=7.7 Hz, 2H)

To a 100 mL flame dried round bottom flask under a nitrogen atmosphere was charged 0.83 g (2.6 mmol) of 4-[(2,6-diamino-4-chloro-5-pyrimidinyl)butyl]benzoic acid dissolved in 20 mL of anhydrous DMF, followed by the addition of 0.45 g (2.6 mmol) of 2-chloro-4,6-dimethoxy-1,3,5-triazine and 0.29 mL (2.6 mmol) of 4-methylmorpholine. The pale yellow solution was stirred at ambient temperature for 30 minutes. Next, 0.65 g (2.7 mmol) of L-glutamic acid diethyl ester hydrochloride was added along with 0.29 mL (2.6 mmol) of 4-methylmorpholine. The reaction mixture was then stirred at ambient temperature for 2.5 hours. The volatiles were removed in vacuo, and the crude residue was dissolved in CHCl₃, washed with brine, dried over Na₂SO₄, and removed in vacuo. The crude solid was then flash chromatographed on silica gel eluting with 5% MeOH/CHCl₃. The correct fractions were collected and the solvents were removed in vacuo to give 0.16 g (12%) of N-{[4-(2,6-diamino-4-chloro-5-pyrimidinyl)butyl]benzoyl}-L-glutamic acid diethyl ester as a white solid.

$R_f$=0.39 (10% MeOH/CHCl₃)
m.p.=125°-128° C.
Mass (FAB) M+1 HRMS=Calcd.: 506.2170; Found: 506.2167
IR (KBr, cm⁻¹)=1204, 1373, 1457, 1542, 1639, 1737, 2932, 3371 UV (EtOH) $\lambda_{max}$=288, 236, 203 ($\epsilon$=6474, 22690, 43250)
¹H NMR (300 MHz, DMSO$_{d6}$) δ1.11-1.25 (m, 6H), 1.37-1.40 (m, 2H), 1.58-1.70 (m, 2H), 1.90-2.15 (m, 2H), 2.41 (t, J=7.2 Hz, 4H), 2.63 (t, J=7.4 Hz, 2H), 3.98-4.20 (m, 4H), 4.35-4.80 (m, 1H), 6.02 (s, 2H), 6.44 (s, 2H), 7.27 (d, J=8.1 Hz, 2H), 7.76 (d, J=8.1 Hz, 2H), 8.61 (d, J=7.4 Hz, 1H)

C. Preparation of N-{[4-(2,6-diamino-4-chloro-5-pyrimidinyl)butyl]benzoyl}-L-glutamic acid

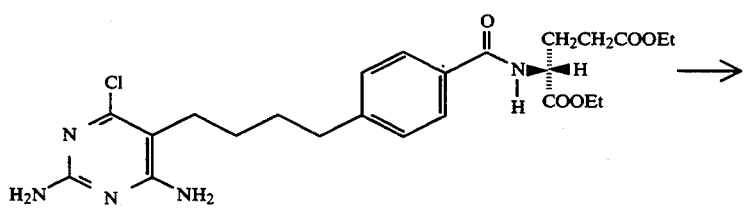

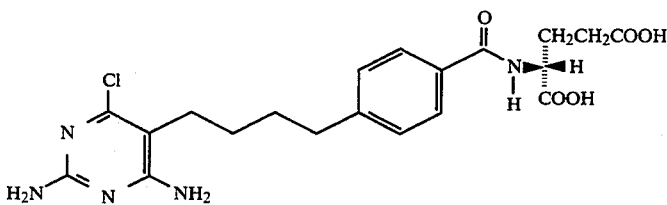

To a 25 mL round bottom flask was charged 0.075 g (0.15 mmol) of N-{[4-(2,6-diamino-4-chloro-5-pyrimidinyl)butyl]benzoyl}-L-glutamic acid diethyl ester dissolved in 4 mL 0.5N NaOH and 1 mL of MeOH. The yellow solution was stirred at ambient temperature for 6 hours. The solution was cooled down in an ice bath and acidified to pH 2 using 5N HCl. The precipitate was filtered, washed with cold water, and dried in a vacuum oven at 60° C. to give 0.039 g (58%) of N-{[4-(2,6-diamino-4-chloro-5-pyrimidinyl)butyl]benzoyl}-L -glutamic acid as a white solid.

$R_f$=0.08 (50% MeOH/CHCl$_3$)

m.p.=198°-200° C.

Mass (FAB) M+1 HRMS=Calcd.: 450.1544; Found: 450.1565

IR (KBr, cm$^{-1}$)=1292, 1636, 3330 UV (EtOH) $\lambda_{max}$=288, 237, 203 ($\epsilon$=4756, 16741, 32509)

$^1$H NMR (300 MHz, DMSO$_{d6}$) $\delta$1.36–1.40 (m, 2H), 1.61–1.63 (m, 2H), 1.92–2.20 (m, 2H), 2.33 (t, J=7.4 Hz, 2H), 2.40 (t, J=7.4 Hz, 2H), 2.63 (t, J=7.4 Hz, 2H), 6.02 (s, 2H), 6.44 (s, 2H), 7.26 (d, J=8.1 Hz, 2H), 7.77 (d, J=8.0 Hz, 2H), 8.49 (d, J=7.6 Hz, 1H)

Example 3

A. Preparation of N-{[4-(2,6-diamino-5-pyrimidinyl)butyl]benzoyl}-L-glutamic acid diethyl ester To a Parr bottle were charged 0.87 g (1.72 mmol of N-{[4-(2,6-diamino-4-chloro-5-pyrimidinyl)butyl]benzoyl}-L-glutamic acid diethyl ester and 0.75 g of 10% Pd/C catalyst in 100 mL of absolute ethanol. The mixture was hydrogenated at 60 psi of hydrogen gas for 5 hours at 60° C. The catalyst was filtered and washed with fresh ethanol, and the filtrate was removed in vacuo. The crude residue was flash chromatographed on silica gel eluting with 10% MeOH/CHCl$_3$ to give 0.32 g (39%) of N-{[4-(2,6-diamino-5-pyrimidinyl)butyl]benzoyl}-L-glutamic acid diethyl ester as a white solid.

$R_f$=0.15 (10% MeOH/CHCl$_3$)

m.p.=60°-62° C.

Mass (FAB) M+1 HRMS=Calcd.: 472.2560; Found: 472.2608

IR (KBr, cm$^{-1}$)=1187, 1455, 1562, 1617, 1736, 2934, 3373 UV (EtOH) $\lambda_{max}$=289, 236, 203 ($\epsilon$=6505, 23358, 41676)

$^1$H NMR (300 MHz, DMSO$_{d6}$) $\delta$1.11–1.19 (m, 6H), 1.38–1.42 (m, 2H), 1.54–1.59 (m, 2H), 1.90–2.15 (m, 2H), 2.25 (t, J=7.0 Hz, 2H), 2.44 (t, J=7.4 Hz, 2H), 2.63 (t, J=7.3 Hz, 2H), 3.99–4.11 (m, 4H), 4.39–4.41 (m, 1H), 5.70 (s, 2H), 6.19 (s, 2H), 7.26 (d, J=8.1 Hz, 2H), 7.43 (s, 1H), 7.76 (d, J=8.1 Hz, 2H), 8.61 (d, J=7.4 Hz, 1H)

B. Preparation of N-{[4-(2,6-diamino-5-pyrimidinyl)-

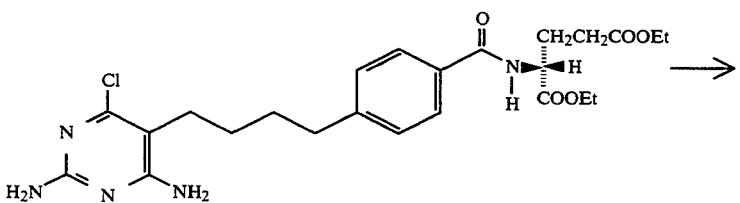

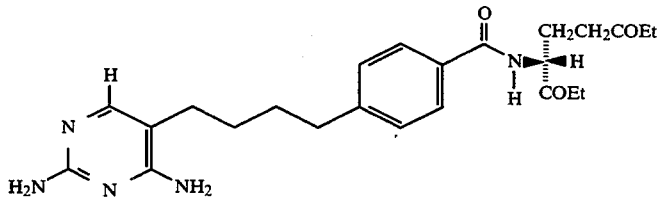

butyl]benzoyl}-L-glutamic acid

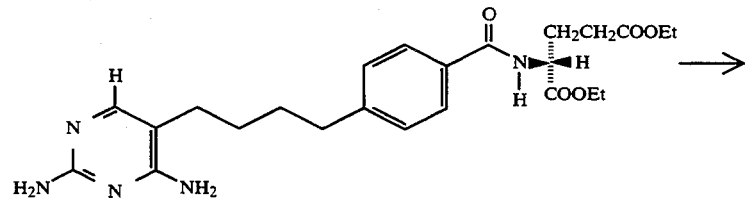

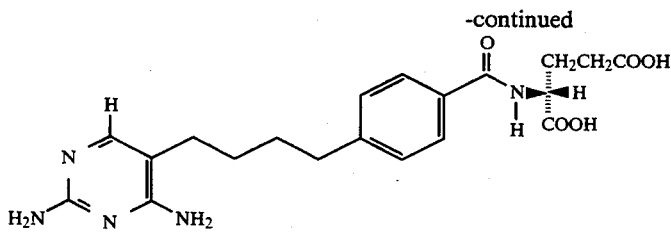

To a 25 mL round bottom flask was charged 0.31 g (0.66 mmol) of N-{[4-(2,6-diamino-4-hydrogen-5-pyrimidinyl)butyl]benzoyl}-L-glutamic acid diethyl ester suspended in 6 mL of 1N NaOH. The mixture was stirred at ambient temperature for 5.5 hours. The yellow solution was cooled in an ice bath, and acidified to pH 3 using 5N HCl. The precipitate formed was filtered, washed with cold water, and dried in a vacuum oven at 70° C. to give 0.25 g (90%) of N-{[4-(2,6-diamino -5-pyrimidinyl)butyl]benzoyl}-L -glutamic acid as a white solid.

$R_f$=0.07 (50% MeOH/CHCl$_3$)
m.p.=170°–173° C.
Mass (FAB) M+1 HRMS=Calcd.: 416.1934; Found: 416.1942
IR (KBr, cm$^{-1}$)=585, 1194, 1533, 1636, 3352 UV (EtOH) $\lambda_{max}$=224, 202 ($\epsilon$=16785, 30191)
$^1$H NMR (300 MHz, DMSO$_{d6}$) δ1.43 (t, J=6.8 Hz, 2H), 1.56 (t, J=6.7 Hz, 2H), 1.85–2.10 (m, 2H), 2.25–2.37 (m, 4H), 2.63 (t, J=7.0 Hz, 2H), 4.34–4.38 (m, 1H), 6.77 (s, 2H), 7–178 (s, 2H) 7.34 (d, J=7.6 Hz, 2H), 7.42 (s, 1H), 7.79 (d, J=7.2 Hz, 2H), 8.49 (d, J=7.5 Hz, 1H)

Example 4

A. Preparation of 4-[(2-amino-4-chloro-6-methyl-5-pyrimidinyl)butyl]benzoic acid

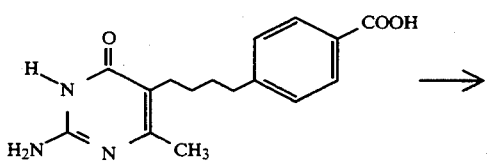

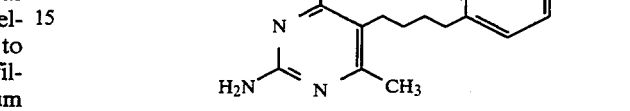

To a 50 mL round bottom flask under a nitrogen atmosphere was charged 1.0 g (3.3 mmol) of 4-[(2-amino-1,6-dihydro-4-methyl-6-oxo-5-pyrimidinyl)butyl]benzoic acid [as taught by Taylor, E. C., et al., Heterocycle, 28(2):1169–1178 (1989)] in 10 mL of phosphorus oxychloride. The reaction mixture was then heated to reflux for 6 hours. After cooling to ambient temperature, the POCl$_3$ was removed in vacuo to near dryness, and this thick residue was slowly poured into a large Erlenmeyer containing ice in a 5% NaHCO$_3$ solution. The pH of the stirring raction mixture was then adjusted to 4 using 5N HCl. The off-white solid was then filtered and dried in a vacuum oven at 50° C. to give 0.67 g (63%) of 4-[(2-amino-4-chloro-6-methyl-5-pyrimidinyl)-butyl]benzoic acid.

$R_f$=0.23 (7: 2.5: 0.5 CHCl$_3$/MeOH/NH$_4$OH)
m.p.=147°–150° C.
Mass (FAB) M+1 HRMS=Calcd: 320.1166; Found: 320.1170
IR (KBr, cm$^{-1}$)=627, 876, 1172, 1211, 1329, 1485, 1535, 1605, 1667, 1738, 1769, 2929, 3318 UV (EtOH) $\lambda_{max}$=296, 237, 202 ($\epsilon$=3818, 24310, 27821)
$^1$H NMR (300 MHz, DMSO$_{d6}$) δ1.41–1.51 (m, 2H), 1.62–1.72 (m, 2H), 2.29 (s, 3H), 2.51–2.75 (m, 4H), 7.10 (br s, 2H), 7.31 (d, J=7.7 Hz, 2H), 7.83 (d, J=8.1Hz, 2H)

B. Preparation of N-{[4-(2-amino-4-chloro-6-methyl-5-pyrimidinyl)butyl]benzoyl}-L-glutamic acid diethyl ester

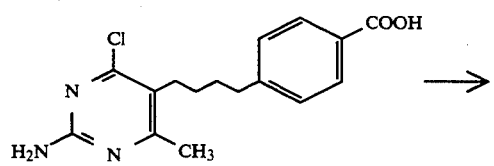

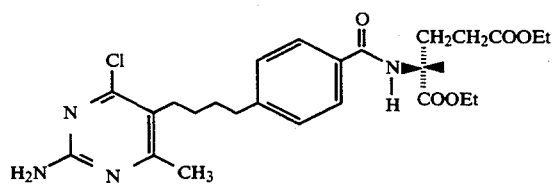

To a 50 mL flame-dried round bottom flask under a nitrogen atmosphere was charged 0.66 g (2.06 mmol) of 4-[(2-amino-4-chloro-6-methyl-5-pyrimidinyl)butyl]-benzoic acid dissolved in 15 mL of anhydrous DMF, followed by the addition of 0.36 g (2.06 mmol) of 2-chloro-4,6-dimethoxy-1,3,5-triazine and 0.23 mL (2.06 mmol) of 4-methylmorpholine. The pale yellow solution was stirred at ambient temperature for 30 minutes. Next, 0.49 g (2.06 mmol) of L-glutamic acid diethyl ester hydrochloride was added along with 0.36 mL (2.06 mmol) of 4-methylmorpholine. The reaction mixture was then stirred at ambient temperature for 3 hours. The volatiles were removed in vacuo, and the crude residue was dissolved in CHCl₃, washed with brine, dried over Na₂SO₄, and removed in vacuo. This solid was then purified using medium pressure liquid chromatography on a Lobar Si 60 (E. M. Merck, Darmstad, Germany) glass column eluting with a gradient of 30:70 EtOAc/MeCl₂ to 75:25 EtOAc/MeCl₂ to give 0.26 g (25%) of N-{[4-(2-amino-4-chloro-6-methyl-5-pyrimidinyl)butyl]benzoyl}-L-glutamic acid diethyl ester as a colorless oil.

R$_f$=0.52 (4% MeOH/CHCl₃)

Mass (FD) M+ =505

IR (KBr, cm$^{-1}$)=759, 922, 1020, 1098, 1165, 1374, 1427, 1469, 1502, 1540, 1569, 1613, 1737, 2977, 3245 UV (EtOH) λ$_{max}$=401, 236, 202 (ε=4284, 29919, 39328) Anal. Calcd. for C₂₅H₃₃N₄O₅Cl: C, 59.46; H, 6.59; N, 11.09. Found: C, 59.21; H, 6.68; N, 10.89.

¹H NMR (300 MHz, DMSO$_{d6}$) δ1.11–1.22 (m, 6H), 1.41–1.48 (m, 2H), 1.59–1.66 (m, 2H), 1.96–2.10 (m, 2H), 2.25 (s, 3H), 2.41 (t, J=7.4 Hz, 3H), 2.47–2.49 (m, 1H), 2.53 (t, J=7.9 Hz, 2H), 3.97–4.12 (m, 4H), 4.36–4.42 (m, 1H), 6.71 (s, 2H), 7.29 (d, J=8.1 Hz, 2H), 7.77 (d, J=8.1 Hz, 2H), 8.62 (d, J=7.4 Hz, 1H)

C. Preparation of N-{4-[(2-amino-6-methyl-5-pyrimidinyl)butyl]benzoyl}-L-glutamic acid diethyl ester

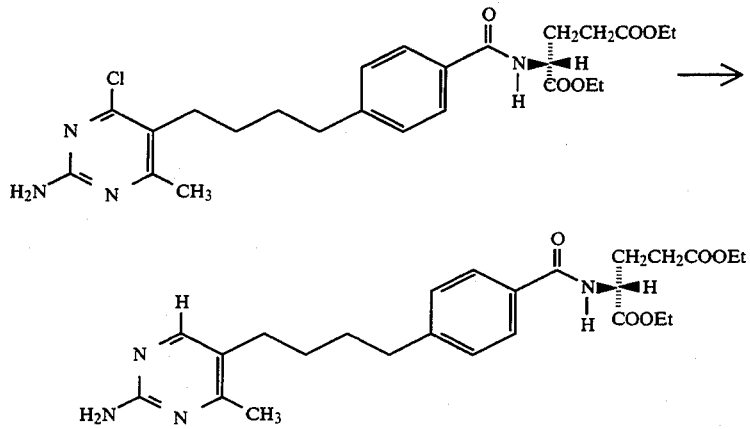

To a 25 mL round bottom flask was charged 0.05 g (0.10 mmol) of N-{[4-(2-amino-4-chloro-6-methyl-5-pyrimidinyl)butyl]benzoyl}-L-glutamic acid diethyl ester dissolved in 4 mL of absolute ethanol with 0.05 mL of concentrated ammonium hydroxide. To this stirring solution was added 0.025 g of 10% Pd/C catalyst. This mixture was then stirred under hydrogen at 1 atmosphere for 1.5 hours. The catalyst was filtered away and washed with fresh ethanol. The filtrate was removed in vacuo, and the crude residue was purified using flash chromatography on silica gel eluting with 4% MeOH/EtOAc to give 0.042 g (90%) of N-{4-[(2-amino-6-methyl-5-pyrimidinyl)butyl]benzoyl}-L-glutamic acid diethyl ester as a white solid.

R$_f$=0.26 (4% MeOH/EtOAc)

m.p.=85°–87° C.

Mass (FAB) M+1 HRMS=Calcd: 471.2607; Found: 471.2607

IR (KBr, cm$^{-1}$)=546, 800, 1021, 1486, 1535, 1663, 1738, 2934, 3337 UV (EtOH) λ$_{max}$=302, 233, 203 (ε=3897, 31177, 32900)

¹H NMR (300 MHz, DMSO$_{d6}$) δ1.11–1.22 (m, 6H), 1.41–1.48 (m, 2H), 1.54–1.61 (m, 2H), 1.98–2.09 (m, 2H), 2.18 (s, 3H), 2.37–2.47 (m, 4H), 2.64 (t, J=7.4 Hz, 2H), 3.30–4.12 (m, 4H), 4.38–4.42 (m, 1H), 6.20 (s, 2H), 7.28 (d, J=8.1 Hz, 2H), 7.77 (d, J=8.1 Hz, 2H), 7.87 (s, 1H), 8.61 (d, J: 7.4 Hz, 1H)

D. Preparation of N-{4-[(2-amino-6-methyl-5-pyrimidinyl)butyl]benzoyl}-L-glutamic acid

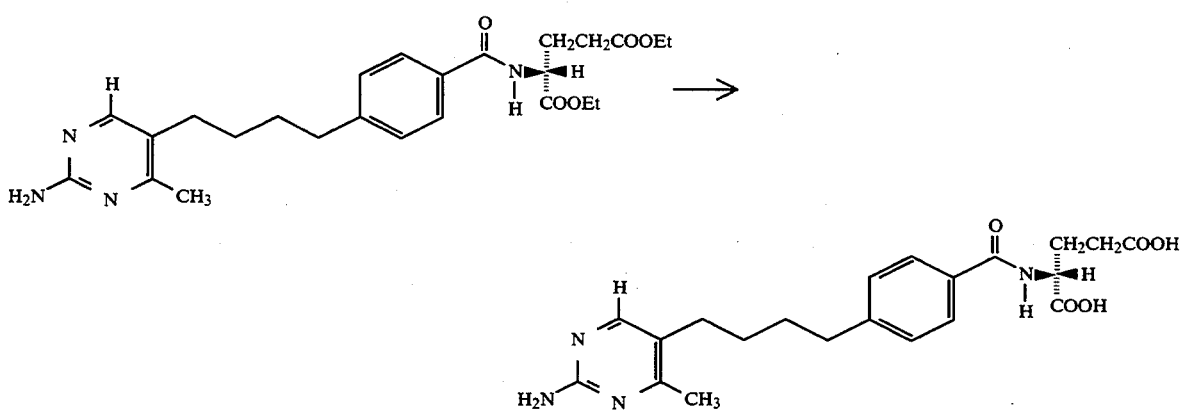

In a 15 mL round bottom flask was suspended 0.030 g (0.064 mmol) of N-{4-[(2-amino-6-methyl-5-pyrimidinyl)butyl]benzoyl}-L-glutamic acid diethyl ester in 2 mL of 1N NaOH and 1 mL of MeOH. After 3 hours a yellow solution formed and the reaction was stirred at ambient temperature for 4 days. The reaction was then acidified to a pH of 3 using 5N HCl. Next the volatiles were removed in vacuo, and the residue was triturated in 2 mL of water in an ice bath. The solid was filtered, washed with cold water; and dried in a vacuum oven at 60° C. to give 0.016 g (61%) of N-{4-[(2-amino-6-methyl-5-pyrimidinyl)butyl]benzoyl}-L-glutamic acid as a white solid.

$R_f$=0.12 (50% MeOH/CHCl$_3$)
m.p. =216°-217° C.
Mass (FAB) M+1 HRMS=Calcd: 415.1981; Found: 415.2003

IR (KBr, cm$^{-1}$)=522, 581, 626, 743, 812, 854, 908, 1104, 1155, 1181, 1232, 1321, 1388,1496, 1527, 1568, 1639, 1668, 1734, 3184, 3420 UV (EtOH) $\lambda_{max}$=302, 233, 202 ($\epsilon$=3529, 27696, 31092)

$^1$H NMR (300 MHz, DMSO$_{d6}$) δ1.44–1.53 (m, 2H), 1.56–1.65 (m, 2H), 1.92–2.08 (m, 2H), 2.32 (t, J=7.5 Hz, 2H), 2.37 (s, 3H), 2.39–2.56 (m, 2H), 2.65 (t, J=7.2 Hz, 2H), 4.34–4.39 (m, 1H), 7.28 (d, J=8.1 Hz, 2H), 7.70 (br s, 2H), 7.78 (d, J=7.2 Hz, 2H), 8.13 ( s, 1H), 8.50 (d, J=7.6 Hz, 1H)

Example 5

A. Preparation of 2,6-dipivaloylamino-5-carboxaldehydepyrimidine

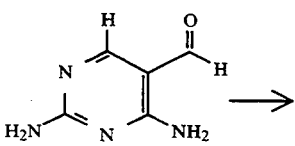

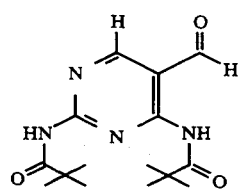

To a 250 mL round bottom flask flame dried under a nitrogen atmosphere was suspended 2.0 g (14.5 mmol) of 2,6-diamino-5-carboxaldehydepyrimidine [as described in J. Med. Chem., 26:667-673 (1983)] in 16 mL of anhydrous DMF, followed by the addition of 16 mL (78.9 mmol) of trimethylacetic anhydride. This mixture was then heated to 160° C. for 1 hours. The dark brown solution was cooled to ambient temperature and the volatiles were removed in vacuo. The crude residue was dissolved in 100 mL of MeCl$_2$ and washed 3 times with 100 mL hot water, dried over Na$_2$SO$_4$, and removed in vacuo. The solid was then flash chromatographed on silica gel eluting with 1:1 EtOAc/MeCl$_2$. The correct fractions were combined and removed in vacuo to give 2.4 g (54%) of 2,6-dipivaloylamino-5-carboxaldehydepyrimidine as a white solid.

$R_f$=0.21 (1:1 EtOAc/MeCl$_2$)
mp.=182°-184° C.
Mass (FAB) M+1 HRMS=Calcd.: 307.1770; Found: 307.1758

IR (KBr, cm$^{-1}$)=802, 836, 1001, 1130, 1208, 1256, 1327, 1370, 1397, 1452, 1485, 1625, 1663, 1718, 2969, 3223, 3511 UV (EtOH) $\lambda_{max}$=291, 248 ($\epsilon$=14,856, 28,220)

$^1$H NMR (300 MHz, CDCl$_3$) δ1.35 (S, 9H), 1.38 (S, 9H), 8.61 (br s, 1H), 8.87 (s, 1H), 9.85 (s, 1H), 11.42 (br s, 1H)

B. Preparation of 4-cyanobenzoyl-L-glutamic acid diethyl ester

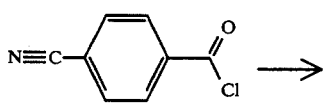

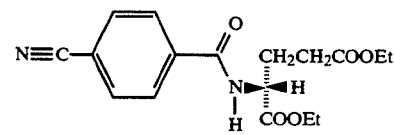

To a 250 mL round bottom flask flame dried under a nitrogen atmosphere was charged 17.4 g (72.5 mmol) of diethyl L-glutamate hydrochloride dissolved in 50 mL of anhydrous MeCl2, followed by the addition of 21.0 mL (151 mmol) of triethylamine. The stirring mixture was then cooled down in an ice bath, and 10.0 g (60.4 mmol) of 4-cyanobenzoyl chloride in 40 mL of anhydrous MeCl$_2$ was added dropwise. After the addition, the ice bath was removed, and the mixture was stirred for 2.5 hours. The reaction mixture was diluted with additional MeCl$_2$, washed with water, dried over Na$_2$SO$_4$, and removed in vacuo. The crude solid was then flash chromatographed on silica gel eluting with 25% EtOAc/MeCl$_2$. After collecting the correct fractions, the solvents were removed in vacuo to give 15.4 g (77%) of 4-cyanobenzoyl-L-glutamic acid diethyl ester as a white solid.

$R_f$=0.59 (25% EtOAc/MeCl$_2$)
m.p.=84°-86° C.
Mass (FD) M+ =332
IR (KBr, cm$^{-1}$)=857, 1021, 1156, 1182, 1206, 1222, 1268, 1322, 1383, 1447, 1502, 1641, 1745, 2235, 3336 UV (EtOH) $\lambda_{max}$=237, 201 ($\epsilon$=18,622, 23,473) Anal. Calcd. for C$_{17}$H$_{20}$N$_2$O$_5$: C, 61.44; H, 6.07; N, 8.43. Found: C, 61.38; H, 6.14; N, 8.44.

$^1$H NMR (300 MHz, cm$^{-1}$) δ1.23–1.35 (m, 6H), 2.18–2.55 (m, 4H), 4.15 (q, J=7.0 Hz, 2H), 4.27 (q, J=7.0 Hz, 2H), 4.74–4.78 (m, 1H), 7.38 (d, J=7.0 Hz, 1H), 7.77 (d, J=8.3 Hz, 2H), 7.95 (d, J=8.2 Hz, 2H)

C. Preparation of 4-aminomethylbenzoyl-L-glutamic acid diethyl ester

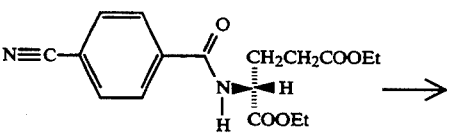

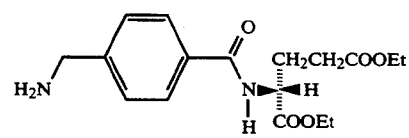

To a Parr bottle were charged 11.1 g (33.4 mmol) of 4-cyanobenzoyl-L-glutamic acid diethyl ester and 1.1 g of 5% Pd/C in 110 mL of glacial acetic acid. The reaction was hydrogenated at ambient temperature for 1.25 hours at 15 psi of hydrogen gas. After filtering and washing the catalyst with fresh acetic acid, the filtrate was removed in vacuo. The residue was dissolved in 1 L of water and washed 3 times with 300 mL of MeCl$_2$. The aqueous layer was neutralized with 5% NaHCO$_3$ until the pH reached 8. The aqueous layer was then extracted 10 times with 200 mL of MeCl$_2$, and the organic layers were combined, dried over Na$_2$SO$_4$, and removed in vacuo to give 9.5 g (82%) of 4-aminomethylbenzoyl-L-glutamic acid diethyl ester as a white solid.

R$_f$=0.44 (25% EtOAc/MeCl$_2$)
m.p.=92°–94° C.
Mass (FD) M+1=337
IR (KBr, cm$^{-1}$)=1156, 1181, 1228, 1308, 1351, 1377, 1418, 1503, 1526, 1611, 1634, 1732, 1749, 2931, 3316, 3396 UV (EtOH) $\lambda_{max}$=237, 203 ($\epsilon$=13917, 23916)
Anal. Calcd. for C$_{17}$H$_{24}$N$_2$O$_5$: C, 60.70; H, 7.19; N, 8.33. Found: C, 60.80; H, 7.16; N, 8.05.

$^1$H NMR (300 MHz, CDCl$_3$) $\delta$1.22–1.35 (m, 6H), 2.13–2.20 (m, 1H), 2.31–2.53 (m, 3H), 3.95 (s, 2H), 4.13 (q, J=7.0 Hz, 2H), 4.26 (q, J=7.0 Hz, 2H), 4.78–4.85 (m, 1H), 7.01 (d, J=7.2 Hz, 1H), 7.42 (d, J=8.2 Hz, 2H), 7.81 (d, J=8.2 Hz, 2H)

D. Preparation N-{[4-aminomethyl-(2,6-dipivaloylamino-5-pyrimidinyl)methyl]benzoyl}-L-glutamic acid diethyl ester the residue was dissolved in 100 mL CHCl$_3$, washed with brine, dried over Na$_2$SO$_4$, and removed in vacuo. The crude was then flash chromatographed on silica gel eluting with 6% MeOH/CHCl$_3$. The correct fractions were collected and removed in vacuo to give 0.098 g (52%) of N-{[4-aminomethyl-(2,6-dipivaloylamino-5-pyrimidinyl)methyl]benzoyl}-L-glutamic acid diethyl ester as an off-white solid.

R$_f$=0.24 (4% MeOH/CHCl$_3$)
m.p=58°–61° C. (dec)
Mass (FAB) M+1 HRMS=Calcd.: 627.3506; Found: 627.3503
IR (KBr, cm$^{-1}$)=1098, 1145, 1184, 1266, 1297, 1370, 1400, 1429, 1482, 1536, 1591, 1650, 1708, 1737, 2873, 2969, 3305 UV (EtOH) $\lambda_{max}$=282,232 ($\epsilon$=6199, 27105)

$^1$H NMR (300 MHz, CDCl$_3$) $\delta$1.20–1.33 (m, 24H), 2.15–2.49 (m, 4H), 3.79 (d, J=2.6 Hz, 4H), 4.11 (q, J=7.0 Hz, 2H), 4.24 (q, J=7.0 Hz, 2H), 4.76–4.80 (m, 1H), 7.11 (d, J=7.3 Hz, 1H), 7.31 (d, J=8.0 Hz, 2H), 7.81 (d, J=8.1 Hz, 2H), 8.28 (s, 1H), 8.41 (s, 1H), 10.84 (s, 1H)

E. Preparation of N-{[4-aminomethyl-(2,6-diamino-5-pyrimidinyl)methyl]benzoyl}-L-glutamic acid

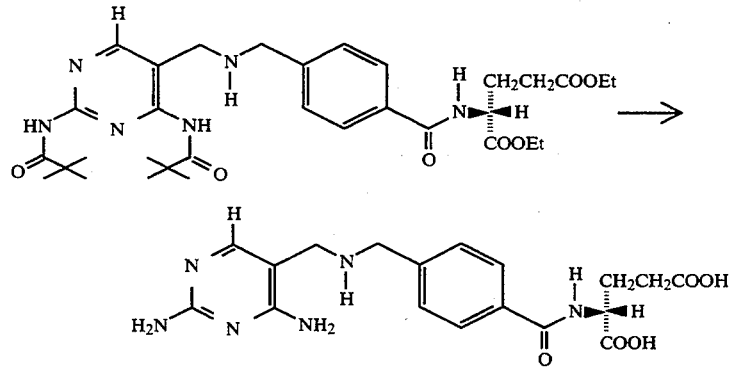

To a 25 mL round bottom flask was suspended 0.11 g (0.17 mmol) of N-{[4-aminomethyl-(2,6-dipivaloylamino-5-pyrimidinyl)methyl]benzoyl}-L-glutamic acid diethyl ester in 4 mL of 1N NaOH and 1

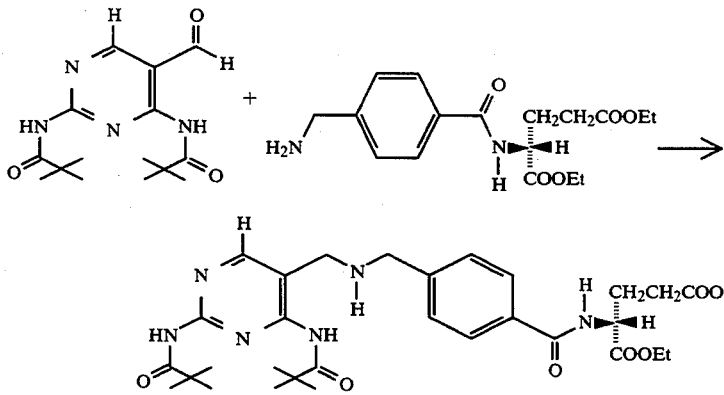

To a 15 mL round bottom flask were charged 0.092 g (0.30 mmol) of 2,6-dipivaloylamino-5-carboxaldehydepyrimidine and 0.10 g (0.30 mmol) of 4-aminomethylbenzoyl-L-glutamic acid diethyl ester dissolved in 2 mL of absolute ethanol. The stirring solution was cooled down in an ice bath, and 0.023 g (0.61 mnmol) of NaBH$_4$ was added portionwise over a 6.5 hour period. The solvent was removed in vacuo, and mL of MeOH. The mixture was stirred at ambient temperature for 4 days. The solution was then acidified to pH 4 using glacial acetic acid. Due to the water solubility of the final product, the volatiles were removed in vacuo, and the solid was dissolved in 4 mL of water and purified in two separate runs utilizing reverse phase high pressure liquid chromatography. A $C_{18}$ semi-prep column with a 5% MeOH/94.5% $H_2O$/0.5% HOAc solvent system was used. The solvents were concentrated in vacuo to a small volume and then lyophilized to give 0.030 g (44%) of N-{[4-aminomethyl-(2,6-diamino-5-pyrimidinyl) methyl]benzoyl}-L-glutamic acid as a white solid.

$R_f$=0.08 (50% MeOH/CHCl$_3$)

m.p.=168°-170° C. (dec)

Mass (FAB) M+1 HRMS=Calcd.: 403.1730; Found: 403.1708

IR (KBr, cm$^{-1}$)=590, 761, 1251, 1399, 1507, 1537, 1668, 3359 UV (EtOH) $\lambda_{max}$=201 ($\epsilon$=13692)

$^1$H NMR (300 MHz, DMSO$_{d6}$) δ1.90–2.06 (m, 1H), 2.28–2.33 (m, 3H), 3.63 (s, 2H), 3.89 (s, 2H), 4.33–4.35 (m, 1H), 6.56 (br s, 2H), 7.08 (br s, 2H), 7.46 (d, J=7.9 Hz, 2H), 7.63 (s, 1H), 7.84 (d, J=8.0 Hz, 2H), 8.55 (d, J=7.5 Hz, 1H)

Example 6

A. Preparation of N-{[4-amino-(2,4-diamino-5-pyrimidinyl)methyl]thienoyl}-L-glutamic acid diethyl ester To a solution of 500 mg (3.62 mmol) of 2,4-diamino-5-pyrimidinecarboxaldehyde (as prepared, for example, via the procedure described by Stuart, et al., supra) in 20 mL of glacial acetic acid was added 1.19 g (3.62 mmol) of N-(4-aminothienoyl)-L-glutamic acid diethyl ester. This solution was stirred at ambient temperature overnight. To this mixture was added 0.18 mL (3.6 mmol) of borane-triethylamine complex and stirring was continued for another 3 hours. The reaction mixture was concentrated in vacuo and the residue was flash chromatographed on silica gel using 10% methanol/chloroform to give 487 mg (30%) of N-{[4-amino-(2,4-diamino-5-pyrimidinyl)methyl]thienoyl}-L-glutamic acid diethyl ester as fine white solid, m.p.=93°-95° C.

B. Preparation of N-{[4-amino-(2,4-diamino-5-pyrimidinyl)methyl]thienoyl}-L-glutamic acid

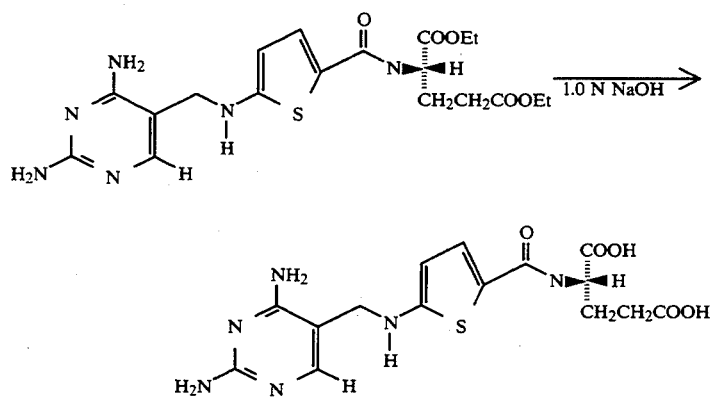

A sample of 100 mg (0.22 mmol) of N-{[4-amino-(2,4-diamino-5-pyrimidinyl)methyl]thienoyl}-L-glutamic acid diethyl ester was treated with 2.0 mL of 1.0N NaOH and was stirred at ambient temperature overnight. The reaction mixture was acidified with 1.0N HCl (pH 3–4) and the precipitate was collected by filtration. The resulting white solid was dried in vacuo to give 37.5 mg (44.4%) of fully unblocked N-{[4-amino-(2,4-diamino-5-pyrimidinyl)methyl]thienoyl}-L-glutamic acid.

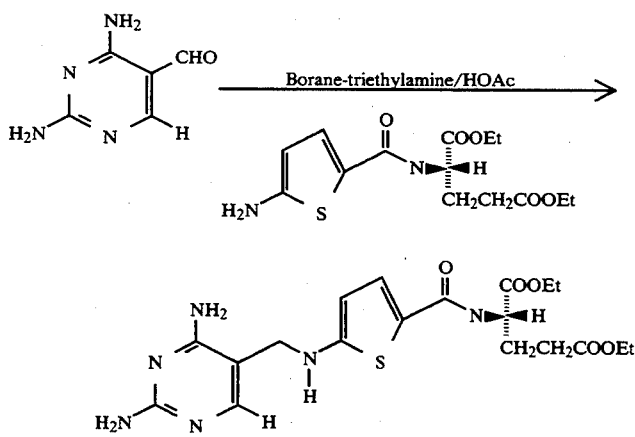

Example 7

A. Preparation of N-{[4-(2,4-diamino-5-pyrimidinyl)ethenyl]benzoyl}-L-glutamic acid diethyl ester

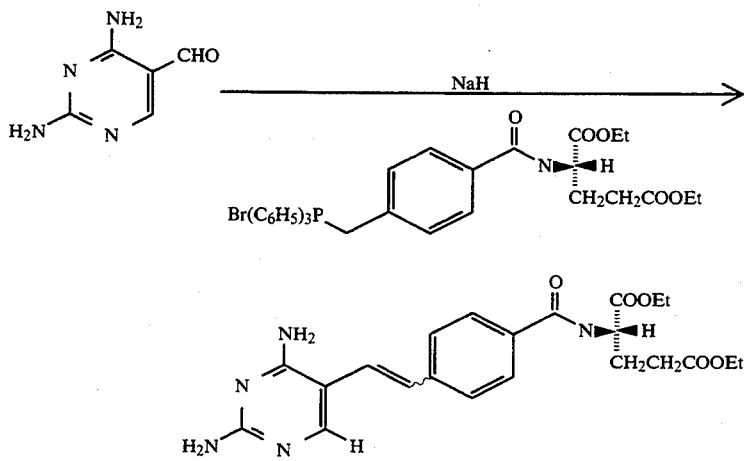

To a suspension of 1.13 g of 60 % NaH in 50 mL of dry DMF was added dropwise a solution of 18.73 g of phosphonium bromide in 200 mL of dry DMF under nitrogen. The yellow colored solution was then stirred at ambient temperature for 2.5 hours before 3.25 g (0.0235 mol) of 2,4-diamino-5-pyrimidinecarboxaldehyde (as prepared, for example, via the procedure described by Stuart, et al., supra) in 50 mL of DMF was added to this solution. The reaction mixture was then stirred at room temperature for 72 hours under nitrogen. Dimethylformamide was then removed in vacuo and the residue was treated with water and extracted with chloroform. The chloroform extract was washed with brine and concentrated in vacuo. The crude residue was chromatographied on silica gel using 2.5% to 10% methanol/chloroform and gave 8.6 g (82.9%) of N-{[4-(2,4-diamino-5-pyrimidinyl)ethenyl]benzoyl}-L-glutamic acid diethyl ester as a white solid.

B. Preparation of N-{[4-(2,4-diamino-5-pyrimidinyl)ethyl]benzoyl}-L-glutamic acid diethyl ester

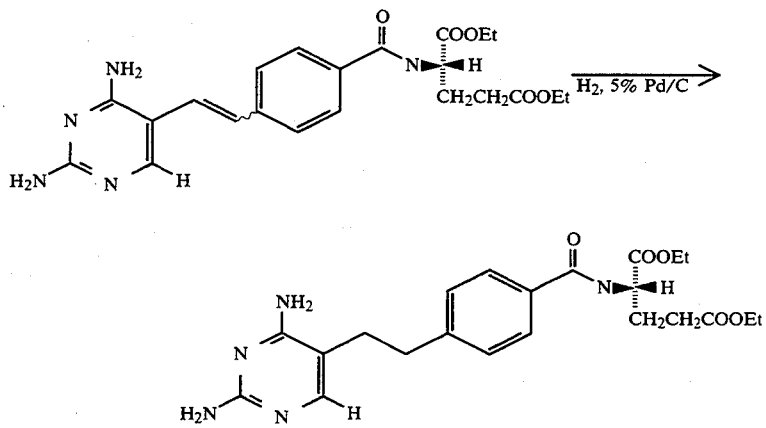

To 100 mg of N-{[4-(2,4-diamino-5-pyrimidinyl)ethenyl]benzoyl}-L-glutamic acid diethyl ester in 5.0 mL of absolute ethanol was added 100 mg of 5% Pd/C and the reaction mixture was stirred under hydrogen atmosphere for 40 hours. The catalyst was removed by filtration through Celite ® and the filtrate was concentrated in vacuo. The residue was then chromatographed on silica gel using 10% methanol/chloroform to give 70 mg (67%) of N-{[4-(2,4-diamino-5-pyrimidinyl)ethyl]benzoyl}-L-glutamic acid diethyl ester as white solid.

C. Preparation of N-{[4-(2,4-diamino-5-pyrimidinyl)ethyl]benzoyl}-L-glutamic acid

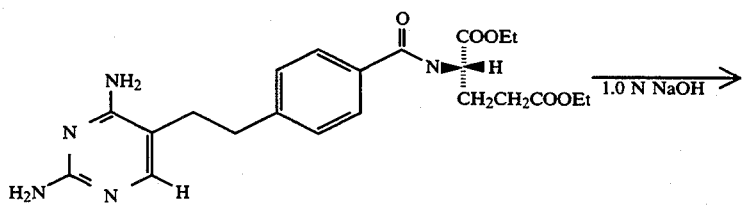

A sample of 54 mg (0.12 mmol) of N-{[4-(2,4-diamino-5-pyrimidinyl)ethyl]benzoyl}-L-glutamic acid diethyl ester was treated with 1.0 mL of 1.0N NaOH and was stirred at ambient temperature overnight. The reaction mixture was acidified with 1.0N HCl (pH 3–4) and the precipate was collected by filtration. The white solid was dried in vacuo to give 28 mg (60%) of unblocked N-{[4-(2,4-diamino-5-pyrimidinyl) ethyl]benzoyl}-L-glutamic acid, m.p.=262° C.

We claim

1. A compound of formula I $$\text{H}_2\text{N}\underset{\text{N}}{\overset{\text{X}}{\bigwedge}}\text{N}\underset{\text{Y}}{\overset{(CH_2)_n-\text{Ⓐ}-CO[NHCH(COOR^1)CH_2CH_2CO]_kOR^1}{}} \quad \text{I}$$

wherein
X is H, bromo, chloro, fluoro, or mercapto;
Y is NH$_2$, or CH$_3$;
n is 2 to 5;
each R$^1$ is H or the same or different carboxy protecting group;
k is 1 to 5; and
Ⓐ is selected from the group consisting of phenyl, thienyl, pyridyl, and furyl, any of which may be optionally substituted with one or two substituent groups selected from halo, hydroxy, C$_1$-C$_4$ alkyl, and C$_1$-C$_4$ alkoxy; or a salt or solvate thereof.

2. A compound according to claim 1 wherein each R$^1$ is the same or different carboxy protecting group and k is 1.

3. A compound according to claim 1 wherein each R$^1$ is H and k is 1.

4. A compound according to claim 1 wherein X is H or chloro; Y is NH$_2$; n is 3 or 4; each R$^1$ is H; and k is 1.

5. A compound according to claim 4 wherein n is 3.

6. A compound according to claim 5 wherein Ⓐ is phenyl, thienyl or furyl.

7. A compound according to claim 6 wherein X is H and Ⓐ is phenyl.

8. A compound according to claim 6 wherein X is chloro and Ⓐ is phenyl.

9. A compound according to claim 4 wherein n is 4.

10. A compound according to claim 9 wherein Ⓐ is phenyl, thienyl, or furyl.

11. A compound according to claim 10 wherein X is H and Ⓐ is phenyl.

12. A compound according to claim 10 wherein X is chloro and Ⓐ is phenyl.

13. A compound according to claim 1 wherein x is H or chloro; Y is NH$_2$; n is 3 or 4; each R$^1$ is the same or different carboxy protecting group; and k is 1.

14. A compound according to claim 13 wherein n is 3.

15. A compound according to claim 14 wherein Ⓐ is phenyl, thienyl, or furyl.

16. A compound according to claim 15 wherein x is H and Ⓐ is phenyl.

17. A compound according to claim 16 wherein each R$^1$ is —CH$_2$CH$_3$.

18. A compound according to claim 15 wherein X is chloro and Ⓐ is phenyl.

19. A compound according to claim 18 wherein R$^1$ is —CH$_2$CH$_3$.

20. A compound according to claim 13 wherein n is 4.

21. A compound according to claim 20 wherein Ⓐ is phenyl, thienyl, or furyl.

22. A compound according to claim 21 wherein X is H and Ⓐ is phenyl.

23. A compound according to claim 22 wherein each R$^1$ is —CH$_2$CH$_3$.

24. A compound according to claim 21 wherein X is chloro and Ⓐ is phenyl.

25. A compound according to claim 24 wherein each R$^1$ is —CH$_2$CH$_3$.

26. A compound of formula V $$\underset{\text{R}^3}{\overset{\text{HN}}{|}}\text{N}\underset{\text{N}}{\bigwedge}\underset{\overset{\text{NH}}{|}}{\text{R}^3}-(CH_2)_i-Q-CH_2-\text{Ⓐ}-CO[NHCH(COOR^1)CH_2CH_2CO]_kOR^1 \quad \text{V}$$

wherein
each R$^1$ is H or the same or different carboxy protecting group;
each R$^3$ is H or the same or different amino protecting group;
i is 1 to 4;
Q is —O—, —S(O)$_j$— (j is 0 to 2), or a group of the formula —NR$^2$— in which R$^2$ is H, C$_1$-C$_4$ alkyl, C$_2$-C$_4$ alkenyl, or C$_2$-C$_4$ alkynyl;
Ⓐ is selected from the group consisting of phenyl, thienyl, pyridyl, and furyl, any of which may be optionally substituted with one or two substituent groups selected from halo, hydroxy, C$_1$-C$_4$ alkyl, and C$_1$-C$_4$ alkoxy; and k is 1 to 5; or a salt or solvate thereof.

27. A compound according to claim 26 wherein each R$^1$ is H; i is 1; Q is a group of the formula —NR$^2$—; R$^2$ is H; each R$^3$ is H; Ⓐ is phenyl; and k is 1.

28. A compound according to claim 26 wherein each $R^1$ is the same or different carboxy protecting group; i is 1; Q is a group of the formula —$NR^2$—; $R^2$ is H; each $R^3$ is the same or different amino protecting group; (A) is phenyl; and k is 1.

29. A compound according to claim 28 wherein each $R^1$ is —$CH_2CH_3$.

30. A compound according to claim 28 wherein each $R^3$ is pivaloyl.

31. A compound according to claim 30 wherein each $R^1$ is —$CH_2CH_3$.

32. A compound of formula III

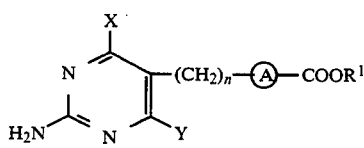

III wherein

X' is bromo, chloro, or fluoro;

Y is $NH_2$ or $CH_3$;

n is 2 to 5;

(A) is selected from the group consisting of phenyl, thienyl, pyridyl, and furyl, any of which may be optionally substituted with one or two substituent groups selected from halo, hydroxy, $C_1$-$C_4$ alkyl, and $C_1$-$C_4$ alkoxy;

and $R^1$ is H or a carboxy protecting group; or a salt or solvate thereof.

33. A compound according to claim 32 wherein X' is chloro; n is 3 or 4; and (A) is phenyl, thienyl or furyl.

34. A compound according to claim 33 wherein (A) is phenyl and $R^1$ is H.

35. A compound according to claim 33 wherein (A) is phenyl and $R^1$ is a carboxy protecting group.

36. A compound according to claim 35 wherein $R^2$ is —$CH_2CH_3$.

37. A pharmaceutical composition comprising a compound according to claim 1 in combination with a pharmaceutically acceptable carrier, diluent or excipient.

38. A method of inhibiting the activity of dihydrofolate reductase in a mammal comprising administering a dihydrofolate reductase inhibiting amount of a compound according to claim 1.

39. A method of treating susceptible neoplasms in a mammal in need of such treatment comprising administering a neoplasm growth inhibiting amount of a compound according to claim 1.

40. A pharmaceutical composition comprising a compound according to claim 26 in combination with a pharmaceutically acceptable carrier, diluent or excipient.

41. A method of inhibiting the activity of dihydrofolate reductase in a mammal in need of such treatment comprising administering a dihydrofolate reductase inhibiting amount of a compound according to claim 26.

42. A method of treating susceptible neoplasms in a mammal in need of such treatment comprising administering a neoplasm inhibiting amount of a compound according to claim 26.

43. A method according to claim 42 wherein said mammal is a human.

* * * * *